US 10,559,384 B2

(12) United States Patent
Peterson et al.

(10) Patent No.: US 10,559,384 B2
(45) Date of Patent: Feb. 11, 2020

(54) DECISION SUPPORT SYSTEM USING INTELLIGENT AGENTS

(71) Applicant: Physio-Control, Inc., Redmond, WA (US)

(72) Inventors: Kenneth J. Peterson, Bellevue, WA (US); Dana Lewis, Woodinville, WA (US); Mitchell Smith, Sammamish, WA (US); Cheryl Protas, Redmond, WA (US); James Wootten, Kirkland, WA (US); David B. Stewart, Carnation, WA (US); Garrett Kotlarchik, Seattle, WA (US); Jeffery Edwards, Bellingham, WA (US); D Craig Edwards, Fall City, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 0 days.

(21) Appl. No.: 16/118,168

(22) Filed: Aug. 30, 2018

(65) Prior Publication Data

US 2018/0374578 A1  Dec. 27, 2018

Related U.S. Application Data

(62) Division of application No. 14/513,961, filed on Oct. 14, 2014, now Pat. No. 10,068,667.
(Continued)

(51) Int. Cl.
*G16H 40/63* (2018.01)
*G16H 50/20* (2018.01)
(Continued)

(52) U.S. Cl.
CPC ............ *G16H 40/63* (2018.01); *A61N 1/046* (2013.01); *G06F 19/00* (2013.01); *G16H 50/20* (2018.01); *G06N 5/025* (2013.01)

(58) Field of Classification Search
CPC ...... A61N 1/3987; A61N 1/3627; A61N 1/39; G06F 19/322; G06F 19/345;
(Continued)

(56) References Cited

U.S. PATENT DOCUMENTS 8,170,980 B1   5/2012 Lulue et al.
8,467,779 B2   6/2013 Helfrich
(Continued)

FOREIGN PATENT DOCUMENTS

WO   0041613 A2   7/2000
WO   0042487 A2   7/2000
(Continued)

OTHER PUBLICATIONS

Tarassenko et al., "Multi-Parameter Monitoring for Early Warning of Patient Deterioration", Biosign(TM), 3rd IEEE International Seminar on Medical Applications of Signal Processing, 2005, 6 pages.

*Primary Examiner* — Manuel A Mendez
(74) *Attorney, Agent, or Firm* — Lane Powell PC

(57) ABSTRACT

A computing architecture, system and method are disclosed for use in a medical device for providing decision support to a caregiver. The computing architecture includes a memory, a processor in communication with the memory, and an instance of a primary rules-based service configured to provide instruction events, the instance providing a primary processing thread of instruction events for coaching treatment of a patient. A software manager module includes an artificial intelligence architecture. The artificial intelligence architecture is configured to provide an instance of a conditional rules-based service for providing instruction events. The instance provided by the artificial intelligence architecture provides a processing thread of instruction events for coaching treatment of a patient that is independent of the primary processing thread and is configured to trigger an
(Continued)

action on the occurrence of a pre-defined set of input conditions.

21 Claims, 21 Drawing Sheets

Related U.S. Application Data

(60) Provisional application No. 61/944,014, filed on Feb. 24, 2014.

(51) Int. Cl.
*A61N 1/04* (2006.01)
*G06F 19/00* (2018.01)
*G06N 5/02* (2006.01)

(58) Field of Classification Search
CPC ... A61B 5/0205; A61B 5/0452; A61B 5/7275; A61B 5/0022; G16H 10/60
See application file for complete search history.

(56) References Cited

U.S. PATENT DOCUMENTS

| | | |
|---|---|---|
| 2006/0112050 A1 | 5/2006 | Miikklainen et al. |
| 2006/0210133 A1 | 9/2006 | Krishnan et al. |
| 2007/0192134 A1 | 8/2007 | Littenberg et al. |
| 2007/0260631 A1 | 11/2007 | Feied et al. |
| 2008/0082358 A1 | 4/2008 | Schmitt et al. |
| 2008/0256490 A1 | 10/2008 | Lord et al. |
| 2010/0293007 A1 | 11/2010 | Schoenberg |
| 2013/0231947 A1* | 9/2013 | Shusterman ........ G06F 19/3418 705/2 |

FOREIGN PATENT DOCUMENTS

| | | |
|---|---|---|
| WO | 0534001 A1 | 4/2005 |
| WO | 0754841 A1 | 5/2007 |
| WO | 0754882 A2 | 5/2007 |
| WO | 0844189 A2 | 4/2008 |
| WO | 1223069 A1 | 2/2012 |

* cited by examiner

DEFIBRILLATION SCENE

| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |

TWO MAIN TYPES OF
EXTERNAL DEFIBRILLATORS

COMPONENTS OF EXTERNAL DEFIBRILLATOR

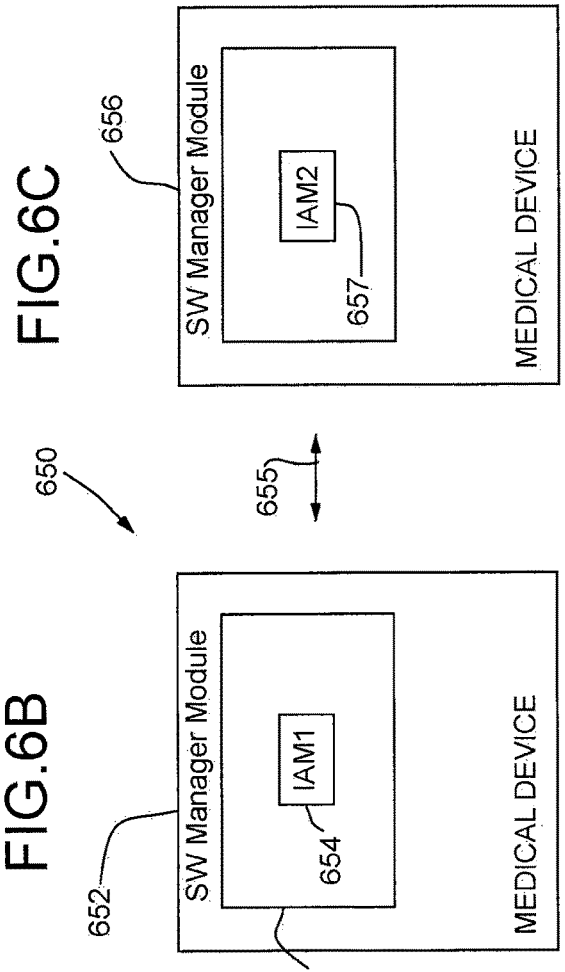
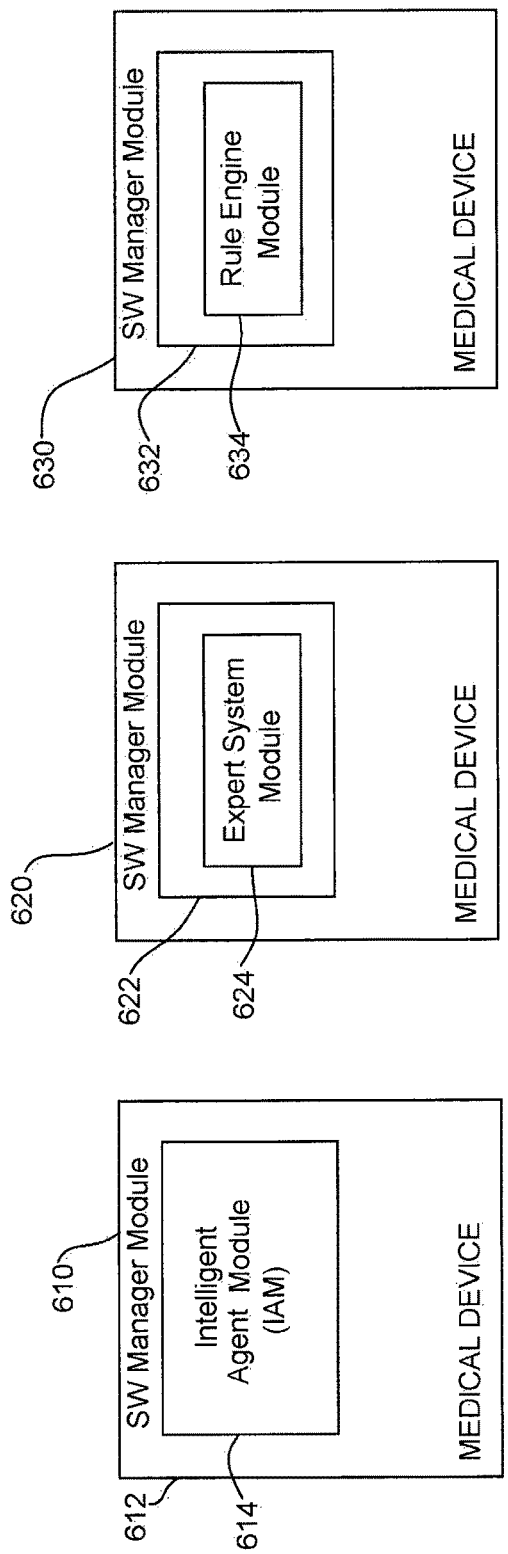
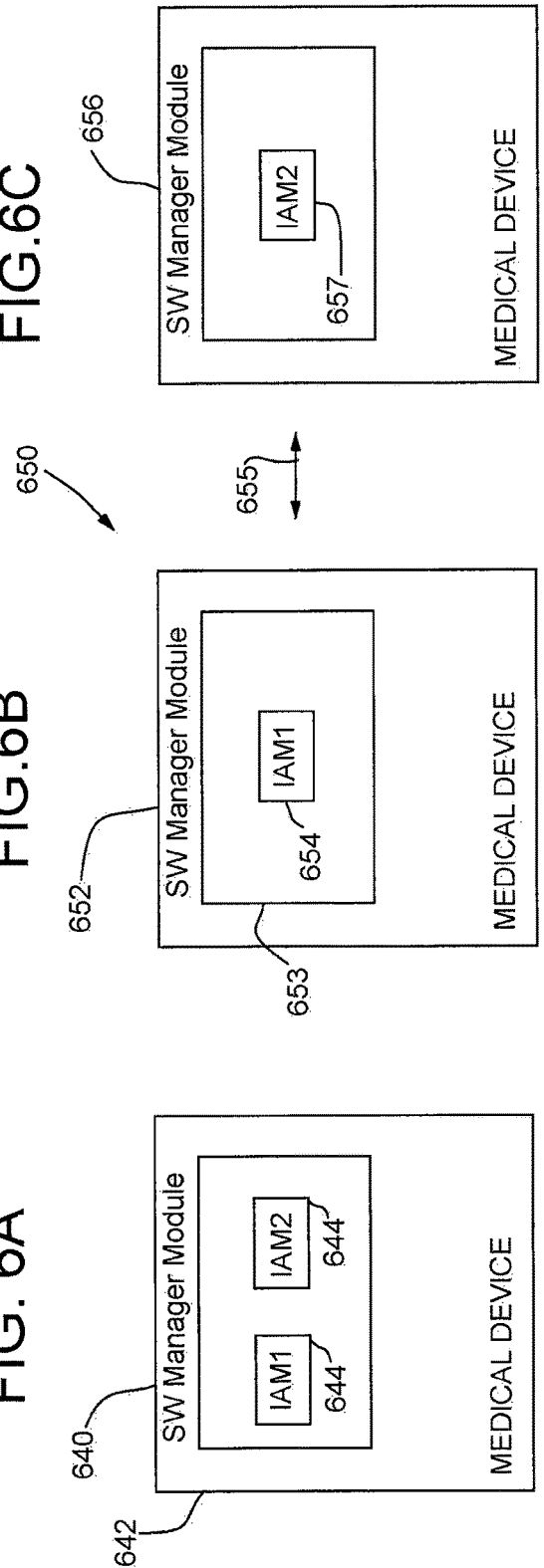

FIG.8 The interrelationship between systemic inflammatory response syndrome (SIRS), sepsis, and infection.

Nursing actions and expected treatment outcomes.

| Treatment | Nursing action | Expected outcomes | Rationale |
|---|---|---|---|
| Fluid replacement | Assess fluid status, monitor CVP Administer 500-ml fluid Challenge every 20-30 minutes | CVP is maintained at 8-12 mm Hg Urine output is >20 ml/h Lungs are clear | EGDT with fluid replacement can improve cardiac output, tissue perfusion, oxygen delivery and survivability in patients with sepsis |
| Control of blood pressure | Monitor MAP Adjust dosage of norepinephrine if MAP <65 mm hg after fluid replacement | MAP is maintained at >65 mm Hg | In EGDT, MAP >65 mm Hg Improved outcomes in patients with sepsis Use of norepinephrine may improve outcomes in patients with sepsis |
| Tissue perfusion | Assess for evidence of adequate Tissue perfusion (eg. Heart rate, respirations, urine output, mentation) Monitor Scvo2 Begin dobutamine infusion if Scvo2<70% after CVP and MAP Corrected Monitor hematocrit | Scvo2 is maintained at >70% Tissue perfusion is adequate as evidenced by urine output >20 mL/h, skin warm/dry, pulses palpable, normal mentation Give blood transfusion if hematocrit <0.30 | EGDT guided by Scvo2 monitoring can reduce mortality in patients with sepsis Improving cardiac output and oxygen delivery to tissues improves outcomes in patients with sepsis |

FIG. 11

| Treatment | Nursing action | Expected outcomes | Rationale |
|---|---|---|---|
| Early treatment with antibiotics 1124 | Ensure that administration of antibiotics begins within 1 hour of patient's entry into the protocol. Begin after samples sent for culturing | Therapy with broad-spectrum antibiotics begins early and treatment is refined according to the results of cultures | Early antibiotic therapy can improve mortality rates in patients with sepsis |
| Administration of steroids for adrenal insufficiency 1125 | Obtain a random blood sample for assay of serum cortisol level and then do a corticotropin stimulation test | Hydrocortisone therapy is started and maintained for patients who do not respond to the corticotropin test | Treatment with low-dose steroids significantly reduces the risk of death in patients with septic shock and adrenal insufficiency |
| Control of blood glucose levels 1126 | Monitor blood glucose levels every hour. Adjust dosage of insulin as needed | Blood glucose level is maintained at 4.4-6.7 mmol/L (80-120 mg/dL) | Tight glycemic control can improve outcomes in critically ill patients |
| Protective lung ventilation 1127 | Monitor and assess patient for evidence of acute organ dysfunction. Identify patients with ALI or ARDS | Patients with evidence of ALI will receive lower tidal volume ventilation. Plateau pressures will be <30 cm $H_2O$ | Lower tidal volume ventilation results in decreased mortality in patients with ALI or ARDS |
| Administration of activated protein C 1128 | Begin administration of activated protein C in eligible patients. Assess patients for signs and symptoms of bleeding. Monitor indicators of coagulation | All eligible patients will receive activated protein C | Treatment with activated protein C improves outcomes in patients with sepsis who have scores >25 on the Acute Physiology and Chronic Health Evaluation II |

Abbreviations: ALI, acute lung injury; ARDS, acute respiratory distress syndrome; CVP, central venous pressure; EGDT, early goal-directed therapy; MAP, mean arterial pressure; Scvo2, central venous oxygen saturation.

FIG. 11
(CONTINUED)

DECISION SUPPORT SYSTEM USING INTELLIGENT AGENTS

CROSS-REFERENCE TO RELATED APPLICATIONS

This application claims priority to U.S. patent application Ser. No. 14/513,961, filed Oct. 14, 2014, now U.S. Pat. No. 10,068,667, issued on Sep. 4, 2018, which claims priority to U.S. provisional patent application No. 61/944,014, filed Feb. 24, 2014, the entire contents of each application incorporated herein by reference.

FIELD

This disclosure generally relates to decision support architectures for medical devices.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body and from where it returns to the right atrium to start the oxygenation-deoxygenation cycle of the blood all over again.

The heart chambers pump because of the heart's electrical control system. More particularly, the sinoatrial (SA) node generates an electrical impulse, which generates further electrical signals. These further signals cause the above-described contractions of the various chambers in the heart to occur in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In an SCA, the heart fails to pump blood effectively, and, if not corrected, can result in death. It is estimated that SCA results in more than 250,000 deaths per year in the United States alone. Further, an SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not corrected in time, will result in death, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume normal contractions in pumping blood. If VF is not terminated, the shock may be repeated, often at escalating energies.

A challenge with defibrillation is that the electrical shock must be administered very soon after the onset of VF. There is not much time to do this since the survival rate of persons suffering from VF decreases by about 10% for each minute the administration of a defibrillation shock is delayed. After about 10 minutes, the rate of survival for SCA victims averages less than 2%.

The challenge of defibrillating early after the onset of VF is being met in a number of ways. First, for some people who are considered to be at a higher risk of VF or other heart arrhythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because the blood flow has stopped. They should receive therapy quickly after the onset of VF or they will die.

For a VF victim without an ICD, a different type of defibrillator can be used, which is called an external defibrillator. External defibrillators have been made portable, so they can be brought to a potential VF victim quickly enough to revive them.

During VF, the person's condition deteriorates because the blood is not flowing to the brain, heart, lungs, and other organs. The blood flow must be restored, if resuscitation attempts are to be successful.

Cardiopulmonary Resuscitation (CPR) is one method of forcing blood to again flow in a person experiencing cardiac arrest. In addition, CPR is the primary recommended treatment for some patients with some kinds of non-VF cardiac arrest, such as a systole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows down the deterioration that would otherwise occur while a defibrillator is being retrieved. For patients with an extended downtime, survival rates are higher if CPR is administered prior to defibrillation.

A defibrillator is one medical device that is used to treat conditions. There are other medical devices including those recognized by the U.S. Food and Drug Administration for use in diagnosing, preventing, or treating disease or other conditions.

Advances in medical devices have included provisioning the medical devices with hardware and software for generating alerts that provide coaching to a caregiver on a medical treatment. For example, a medical device may issue instruction events, and even prompts, for the caregiver to perform CPR more effectively. Advanced medical devices may also provide a caregiver with advanced coaching instructions on specific procedures to follow for treating a patient for various conditions such as sepsis, infection, bacteremia, SIRS, trauma, burns, pancreatitis, etc. Many advanced medical devices employ decision trees for navigating a caregiver through the many and varied instructions that may make up a protocol for the treatment of a particular condition of the patient. Caregivers may benefit from enhancements to these and other decision support instructions and alerts that may make the coaching of a caregiver provided by the medical device more effective, efficient, and strategic.

BRIEF SUMMARY

This disclosure is directed generally to providing intelligent agents for a decision support system thereby enhancing analysis through linking and sharing information using knowledge and experience distributed among intelligent agents and caregivers.

More specifically, a medical device includes a computing architecture including a memory, a processor, an instance of a primary rules-based service, and a software manager module including an artificial intelligence architecture. The processor is in communication with the memory. The instance of a primary rules-based service is configured to provide instruction events, the instance providing a primary processing thread of instruction events for coaching treatment of a patient. The artificial intelligence architecture of the software manager module is configured to provide an instance of a conditional rules-based service for providing instruction events. The instance of the artificial intelligence architecture provides a processing thread of instruction events for coaching treatment of a patient that is independent of the primary processing thread and is configured to trigger an action on the occurrence of a pre-defined set of input conditions.

A medical system of this disclosure includes a medical device including a computing architecture, an instance of a primary rules-based service, a software manager module including an artificial intelligence architecture, and an external utility. The medical device includes a computing architecture that includes a memory, a processor in communication with the memory; and a communication module. The instance of a primary rules-based service is configured to provide instruction events, the instance providing a primary processing thread of instruction events for coaching treatment of a patient. The artificial intelligence architecture of the software manager module is configured to provide an instance of a conditional rules-based service for providing instruction events. The instance of the artificial intelligence architecture provides a processing thread of instruction events for coaching treatment of a patient that is independent of the primary processing thread and is configured to trigger an action on the occurrence of a pre-defined set of input conditions. The external utility is configured for communication with the medical device for exchanging data between the medical device and the external utility.

A method of this disclosure provides decision support for a medical treatment. A primary processing thread of instruction events based on a primary rules-based service is provided for coaching treatment of a patient. A processing thread of instruction events that is independent of the primary processing thread for coaching treatment of a patient and based on a conditional rules-based service is provided by an artificial intelligence architecture for coaching treatment of a patient. The processing thread of instruction events based on a conditional rules-based service provided by an artificial intelligence architecture triggers an action on the occurrence of a pre-defined set of input conditions.

These and other features and advantages of this description will become more readily apparent from the following Detailed Description, which proceeds with reference to the drawings, in which:

BRIEF DESCRIPTION OF THE DRAWINGS

FIGS. 6A-6F show illustrative embodiments of a medical device including a computing architecture of this disclosure.

FIG. 11 shows a prior art protocol for the detection and management of sepsis.

DETAILED DESCRIPTION

Figures 1, 2:
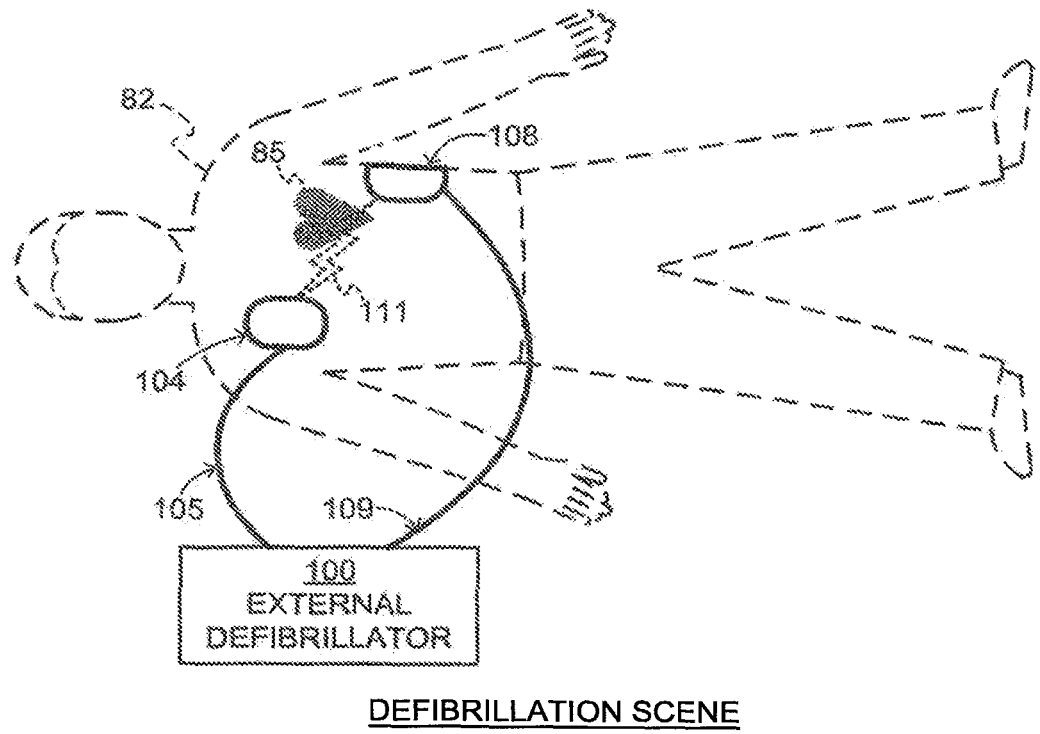
FIG. 1 is an illustrative diagram of a scene showing the use of an external defibrillator to save the life of a person according to this disclosure.
FIG. 2 is a table listing two illustrative types of the external defibrillator shown in FIG. 1, and by whom they might be used.

FIG. 1 is a diagram of a defibrillation scene showing the use of an external defibrillator to save the life of a person according to this disclosure. As shown, a person 82 is lying on his back. Person 82 could be a patient in a hospital, or someone found unconscious, and then turned over onto his back. Person 82 is experiencing a condition in their heart 85, which could be Ventricular Fibrillation (VF).

A portable external defibrillator 100 has been brought close to person 82. At least two defibrillation electrodes 104, 108 are typically provided with external defibrillator 100, and are sometimes called electrodes 104, 108. Electrodes 104, 108 are coupled together with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, also goes through heart 85, in an attempt to restart it, for saving the life of person 82.

Defibrillator 100 can be one of different types, each with different sets of features and capabilities. The set of capabilities of defibrillator 100 is determined based upon who would use it and what training they would be likely to have. Examples are now described.

FIG. 2 is a table listing two typical types of external defibrillators, and who they are primarily intended to be used by. A first type of defibrillator 100 is generally called a defibrillator-monitor, because the defibrillator part is typically formed as a single unit with a patient monitor part. A defibrillator-monitor is sometimes called monitor-defibrillator. A defibrillator-monitor is intended to be used by persons in the medical profession, such as doctors, nurses, paramedics, emergency medical technicians, etc. who may be trained to provide medical treatment to the patient during a defibrillation process based upon information provided by the monitor. Such a defibrillator-monitor is intended to be used in a pre-hospital or hospital scenario.

The defibrillator part may be dedicated to a particular mode of operation. Alternatively, the defibrillator part may be configured to operate in more than one modes of operation. One mode of operation of the defibrillator part may be that of an automated defibrillator, which can determine whether a shock is needed and, if so, charge to a predetermined energy level and instruct the user to administer the shock. Another mode of operation may be that of a manual defibrillator, where the user determines the need and controls administering the shock. In this embodiment, one illustrative defibrillator is configured to enable both automated defibrillation and manual defibrillation modes of operation depending upon the selection of the user. As a patient monitor, the device has features additional to what is minimally needed for mere operation as a defibrillator.

These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (Sp02), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not trained in the medical profession. More particularly, an AED can be used by many professional first responders, such as policemen, firemen, etc. Even a person with only first-aid training can use one. And AEDs increasingly can supply instruction events to whoever is using them. AEDs are thus particularly useful, because it is so critical to respond quickly, when a person suffers from VF. Often, the people who will first reach the VF sufferer may not be in the medical profession.

Increasing awareness of the short survival time of a patient experiencing a VF, has resulted in AEDs being deployed more pervasively in public or semi-public spaces, enabling members of the public to use one provided they have obtained first aid and CPR/AED training. In this way, defibrillation can be administered sooner after the onset of VF, to hopefully be effective in rescuing the person.

There are additional types of external defibrillators, which are not listed in FIG. 2. For example, a hybrid defibrillator can have aspects of an AED, and also of a defibrillator-monitor. An illustrative example may be an AED provided with an ECG monitoring capability.

Figure 3:
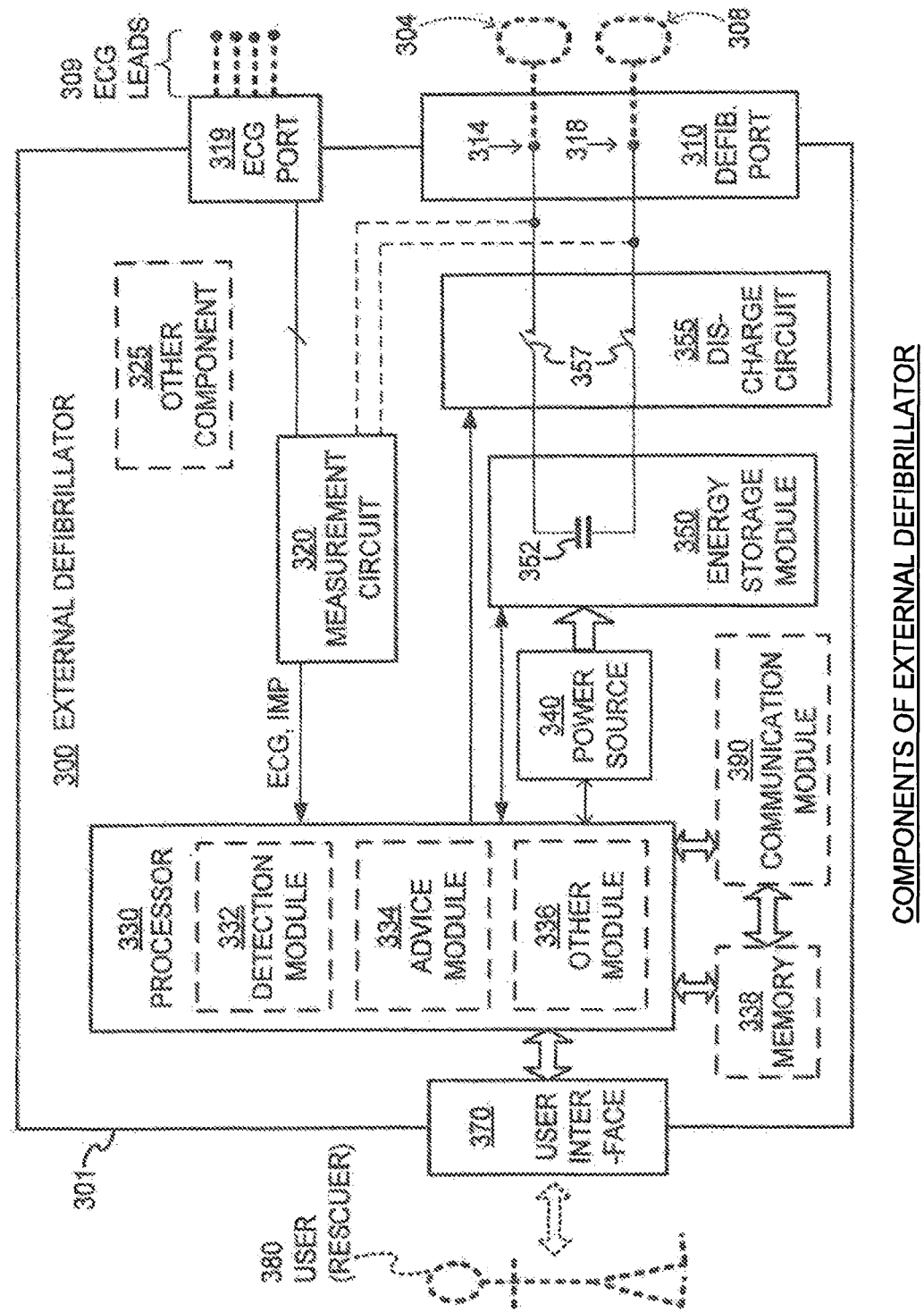
FIG. 3 is a diagram showing components of an external defibrillator, such as the one shown in FIG. 1, configured in an illustrative embodiment according to this disclosure.

FIG. 3 is a diagram showing components of an external defibrillator 300 configured in an illustrative embodiment according to this disclosure. These components can be configured, for example, in external defibrillator 100 of FIG. 1. Plus, these components of FIG. 3 can be provided in a housing 301, which is also known as casing 301.

External defibrillator 300 is intended for use by a user 380, who would be the rescuer. Defibrillator 300 typically includes a defibrillation port 310, which may be configured as a socket (not shown) in housing 301. Defibrillation port 310 includes nodes 314, 318. Defibrillation electrodes 304, 308, which can be similar to electrodes 104, 108 in FIG. 1, can be plugged into defibrillation port 310, so as to make electrical contact with nodes 314, 318, respectively. It is also possible that electrodes can be hard-wired to defibrillation port 310, etc. Either way, defibrillation port 310 can be used for guiding to person 82 via electrodes an electrical charge that has been stored in defibrillator 300, as discussed below.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or a signal taken from a different number of leads. Moreover, a defibrillator-monitor could have additional ports (not shown), and another component 325 for the above described additional features, such as for receipt of patient signals.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals in this case through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 may include a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at a piece of instructional advice based on outputs of detection module 332. Advice module 334 can include a Shock Advisory Algorithm residing in a memory unit (not shown) in the advice module for instructing the processor to implement decision rules, etc. Alternatively, the Shock Advisory Algorithm may reside in part or in whole on a memory 338 of the defibrillator. The instruction to the processor can be to shock, to not shock, to administer other forms of therapy, and so on. If the instruction to the processor is to shock, in some external defibrillator embodiments, the processor is configured to report that instruction to the user via user interface 370, and to prompt the user to do it. In other embodiments, the processor may be configured to execute the instructional advice, by administering the shock. If the instructional advice is to administer CPR, the processor may be configured to enable defibrillator 300 to issue prompts to administer CPR, etc.

Processor 330 can include additional modules, such as module 336, for other functions. In addition, if other component 325 is provided, it may be operated in part by processor 330 or by another processor.

Defibrillator 300 optionally further includes the memory 338, which can work together with processor 330. Memory 338 may be implemented in any number of ways. Such ways include, by way of example and not of limitation, nonvolatile memories (NVM), read-only memories (ROM), random access memories (RAM), any combination of these, etc. Memory 338, if provided, may include programs containing instruction events for execution by processor 330 or other processors that may be included in the external defibrillator. The programs provide instruction events for execution by the processor 330, and can also include instruction events regarding protocols and decision making analytics, etc. that can be used by advice module 334. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include an AC power override, whereby AC power, instead of power from power source 340 is delivered to an energy storage module 350 when AC power is available. In some embodiments, power source 340 is controlled by processor 330.

Defibrillator 300 additionally includes the energy storage module 350. Module 350 is where electrical energy is stored in preparation for a sudden discharge to administer a shock. The charge to module 350 from power source 340 to the right amount of energy can be controlled by processor 330. In typical implementations, module 350 includes one or more capacitors 352, and may include other circuitry.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and in other ways well known in the art.

Defibrillator 300 further includes the user interface 370 for user 380. User interface 370 can be made in any number of ways. For example, interface 370 may include a screen, to display a parameter of a patient that is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other devices. Such communication can be performed wirelessly, or via wire, or by infrared communication, and so on. In this way, data can be communicated from the defibrillator 300 to external devices, such as patient data, incident information, therapy attempted, CPR performance, and so on.

The defibrillator device just described provides one illustrative medical device that may be used with this disclosure. There are other medical devices that may be used with this disclosure including those recognized by the U.S. Food and Drug Administration for use in diagnosing, preventing, or treating disease or other conditions.

In the treatment of a patient, information of a patient, such as conditions of the patient, temperature, pulse rate, visible signs of injury, trauma, etc., or other conditions of the body, may be observed or detected by the caregiver. The caregiver may use that information to take some corrective measure such as administering a treatment to the patient. The feedback response of the patient to the treatment is observed or detected by the caregiver and the caregiver may respond to this feedback by taking further corrective measures. This process of making corrective measures may continue until a point is reached where further corrective measures are no longer required.

In more sophisticated treatment system, a medical device, such as a defibrillator described above and which may be instrumented with ECG or other instrumentation may be used to provide a medical treatment. The medical device may obtain patient parameter data which may include one or more of the following measurements: a measurement of $CO_2$ exhaled by a patient; an electrical activity of the heart of a patient; an exchange of air between the lungs of a patient and the atmosphere; a pressure of the blood in a patient; a temperature of a patient; an oxygen saturation in the blood of a patient; a chest compression of a patient; an image of the internal structure of a patient; an oxygen saturation in the blood in the brain of a patient; the acidity or alkalinity of fluids in a patient; or other patient parameter.

The patient parameter of the $CO_2$ exhaled by a patient may be measured using capnography techniques. The patient parameter of the electrical activity of the heart of a patient may be measured using ECG techniques. The patient parameter of the exchange of air between the lungs of a patient and the atmosphere may be measured using ventilation techniques. The patient parameter of the measurement of the pressure of the blood in a patient may be measured using non-invasive blood pressure measurement techniques or invasive blood pressure measurement techniques. The patient parameter of the temperature of a patient may be measured using temperature measurement techniques. The patient parameter of the oxygen saturation in the blood of a patient may be measured using pulse oximeter techniques or tissue oximetry techniques. The patient parameter of the chest compression of a patient may be measured using chest compression detection and feedback techniques. The patient parameter of the image of the internal structure of a patient may be measured using ultrasound measurement techniques. The patient parameter of the oxygen saturation in the blood in the brain of a patient may be measured using cerebral oximetry techniques. The patient parameter of the acidity or alkalinity of fluids in a patient may be measured using non-invasive pH measurement techniques. These and other techniques and modules for generating the foregoing and other kind of patient parameter data for use with this disclosure are well known in the art. Medical devices may provide a caregiver with certain patient parameter or other data. A caregiver may use this data along with information of a patient that the caregiver may observe or detect, such as conditions of the patient, temperature, pulse rate, visible signs of injury, trauma, etc., or other condition of the body, in performing a treatment on a patient.

Medical devices may also be provided with hardware and software configured to provide a protocol of events that has been programmed into the medical device for the purpose of providing events for coaching the caregiver on a treatment to be administered to the patient. The protocol of events may define a decision tree of events that a caregiver should follow for administering a particular treatment.

Figure 4:
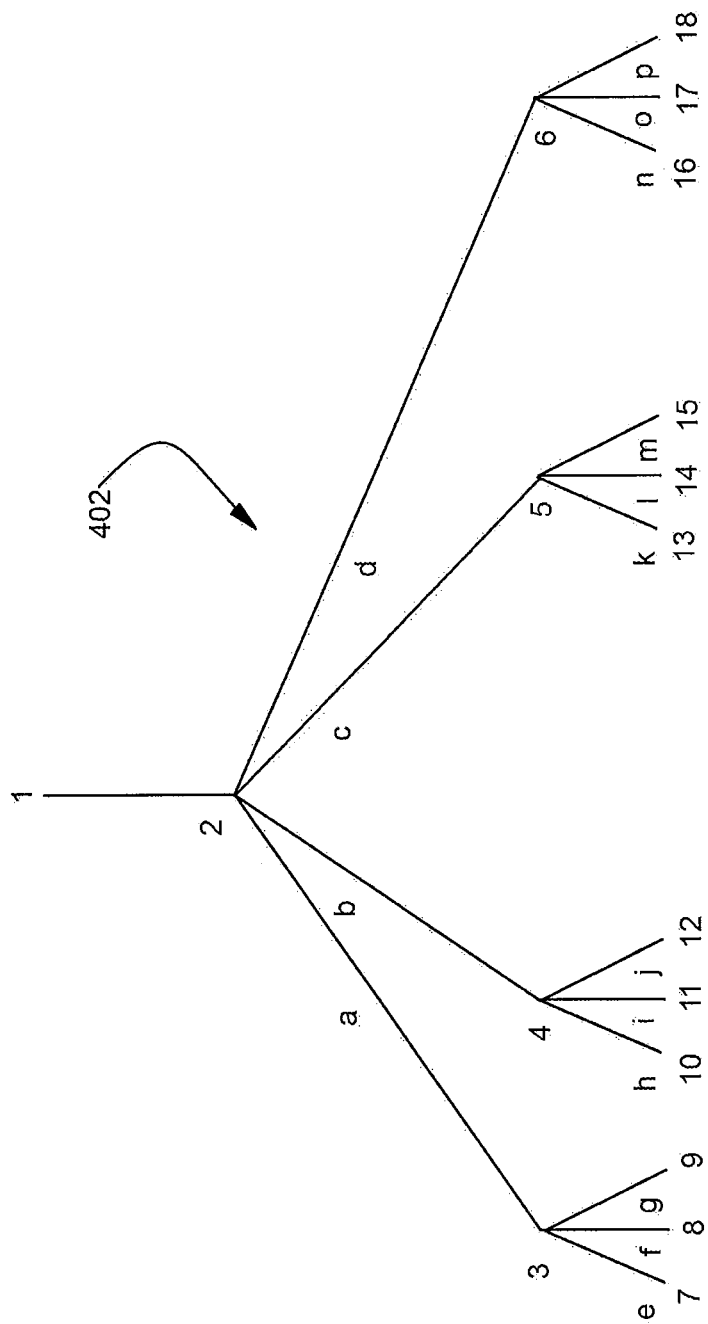
FIG. 4 is an illustration of a prior art decision tree for the treatment of a patient.

FIG. 4 shows a decision tree 401 for an illustrative prior art protocol 402 by a user. The protocol defines a decision tree of events or rules 1-18. Rule 1 may be a selection of the protocol by the user. Each internal (non-leaf) node or rule 2-6 denotes a test on an attribute. Each branch or expected outcome a-p represents the outcome of a test provided by the rules 2-6. Each leaf (or terminal) node 7-18 holds a class label which is the label for the treatment. By way of example, rule 2 provides 4 branches or expected outcomes which might be a protocol treatment for treating infection a, a protocol treatment for treating sepsis b, a protocol treatment for treating trauma c, and a protocol treatment for treating sirs d. Each of branches a-d lead to new rules 3-6, respectively, which in turn lead to branches or expected outcomes which might be protocol treatments e-p. Nodes 7-18 represent the end of the protocol which is the ultimate expected outcome and the label for the treatment.

In practice, a protocol may be initiated by caregiver selection of some branch in the decision tree. The decision tree then typically navigates through the branches of the decision tree based upon that selection. More specifically, a processor of the medical device executes the protocol to create a processing thread of instructions that navigates through the decision tree. Based on the tests performed at the nodes of the tree, the processing thread may issue instructions, alerts, etc., to coach the caregiver through a medical treatment. These and other like decision tree constructs provide a decision support system to a caregiver.

Decision support systems have been enhanced in several ways. In some instances, the decision support system may be dedicated to treatment of a particular medical condition in which case the medical device may be provided with more specialized treatment instructions. In others, the decision support system may be configured to interact with a caregiver such as by waiting on input from a caregiver before issuing the next instruction. This allows the decision support system to factor the feedback or other input of a caregiver into the next instructions, alerts, etc. provided by the decision support system. In other cases, the feedback or other input of a caregiver may be used to modify decision rules implemented by the decision support system. These systems automatically select clinical guidelines applicable to the care of a patient and track the progress of the patient through a stage of the guideline.

Having thus introduced background on the general operation of decision support systems for use with medical devices, we now turn to features that are provided by this disclosure.

A computing architecture, system and method are disclosed for use in a medical device for providing decision support to a caregiver. The computing architecture includes a memory, a processor in communication with the memory, and an instance of a primary rules-based service configured to provide instruction events. The instance provides a primary processing thread of instruction events for coaching treatment of a patient. A software manager module includes an artificial intelligence architecture. The artificial intelligence architecture is configured to provide an instance of a conditional rules-based service for providing instruction events. The instance of the artificial intelligence architecture provides a processing thread of instruction events for coaching treatment of a patient that is independent of the primary processing thread and is configured to trigger an action on the occurrence of a pre-defined set of input conditions.

The following decision support definition terminology taxonomy is provided in support of this disclosure.

Decision Support Definitions are what a customer creates using a Decision Support Definition Editor, as defined below, to have all kinds of customer programmable ("Customer Programmable") help objects such as checklist, messages, reference material, smart algorithms ("Smart Algorithms"), drug calculators ("Drug Calculators"), etc. displayed on the user interface of a customer's medical device(s) ("Customer's Medical Devices") and Medical Device Software Applications, defined below, when a pre-defined set of inputs ("Entrance Criteria") is received. The Decision Support Definitions are made up of Decision Support Definition Sets and Software Managers, as defined below.

The Decision Support Definition Sets are what the Decision Support Definition Editor creates and loads into a user's medical device(s) ("User's Medical Devices") to work in conjunction with Software Managers contained within those devices to create the functionality of the Decision Support Definitions. These Decision Support Definition Sets include the following types which are defined below: Intelligent Agents, Presentation Definitions, Output Definitions, Reference Material, and Smart Algorithms.

Intelligent Agents encapsulate an entrance criteria ("Entrance Criteria") definition and execute concurrently with the Software Managers that control the presentation to the users.

Presentation Definitions inform the Software Managers how to display customized user information based on pre-defined presentation tablets ("Presentation Templates").

Output Definitions inform the Software Managers what output messages to create when the user selects each input on a user interface ("User Interface") defined by the Presentation Definitions.

Reference Material is information (text and graphics) that can be displayed on the User Interface of one of the devices in the disclosed system. The Decision Support Definition Editor can decide when Reference Material is displayed on a device in the system.

Smart Algorithms are individual software algorithms that calculate a new output based on a pre-defined set of patient data inputs. Examples of Smart Algorithms include Smart Vital Indices, Drug Dosage Calculators, and Count-down Timers. The Decision Support Definition Editor can decide when Smart Algorithms are initiated on a device in the system. The output can be used as entrance criteria for the Intelligent Agents.

The Software Managers that make up the Decision Support Definitions are software processes that independently operate within the Medical Device to perform some type of transformation. There could be one or many Software Managers operating within the Medical Device.

External System Elements are the systems that interface with the Decision Support Definition Editor to successfully implement the Decision Support Definitions. The External System Elements include the following elements which are defined below: Decision Support Definition Library, Device Definition Library, Web (World Wide Web), Monitor or Monitor/Defibrillator, and Medical Device Software Applications.

The Decision Support Definition Library is a collection of Decision Support Definitions created and used by the customers of the system. Some of these are designated as shared and available to be review and edited by all customers of the System. The Library can be hosted on a central server ("Central Server") or distributed across multiple storage mechanisms owned by the various customers.

The Device Definition Library contains the software and configuration data of the customer devices. The library can exist on a central server or locally managed on customer device. They capture the data as registered and updated version of each device owned by customers. They verify the configuration information is correct before updating to the latest set of Decision Support Definitions by uploading the Decision Support Definition Software Sets from the Decision Support Definition Editor.

The Web (World Wide Web) is a Repository of shared material ("Shared Material") external to the Medical Device, such as for reference material ("Reference Material") that could be edited and downloaded in the Customer owned devices.

The Monitor or Monitor/Defibrillator is one class of Medical Device that Decision Support Definitions can be deployed on to provide the Customer's programmable help objects. The Software Managers running on the Monitor use the Decision Support Definition Software Sets to determine how to implement the Decision Support Definitions.

Medical Device Software Applications are Medical device software that runs on hardware ("HW") such as Tablet or Laptop computers, Smart Phones, or other Mobile Devices that contain Software Managers that use the Decision Support Definitions to provide the Customer's programmable help objects.

The Decision Support Definition Editor is what the Customer uses to create the Decision Support Definitions that are used by the Software Managers on the customer's devices. It is made up of the following functions (these could be implemented in a variety of ways) defined below: a Directory Viewer and an Editor.

The Directory Viewer is used to create new or view and manage the previously generated Decision Support Definitions that are stored on the Decision Support Definition Library.

The Editor modifies the Decision Support Definitions. It is made up of the following functions. These could be implemented in a variety of ways including a Version Control (check-in/check-out), an Entrance Criteria (Intelligent Agent), and a display generator ("Display Generator") ("Display Manager").

The Version Control (check-in/check-out) assigns the name and version number to the Decision Support Definitions that are being edited and what device type and group the Decision Support Definitions are allocated to.

The Entrance Criteria (Intelligent Agent) defines the entrance criteria necessary to trigger the Decision Support Definitions.

The Display Generator (Display Manager) uses the user Interface templates in the Template Library to define the User Interface Presentation of the Decision Support Definition on the associated device type.

The Result Generator (Response Manager) determines the outputs generated from each user interface control ("User Interface Control") on the Display Generator.

The Smart Algorithms determine the transformation of available inputs to outputs. The customer has the ability to edit what a smart algorithm produces based on available inputs.

Device Definition Sets Manager provides an interface into the Device Definition Library to identify all devices that have been registered by the customer and place those devices into groups for application of the Decision Support Definitions. It also allows updates to the Device Definition Data to be uploaded to the Device Definition Library.

Template Library provides the pre-defined user interface templates ("User Interface Templates") that are already supported by the Software Managers that operate on the various devices that make up the System.

Decision Support Definition Set Generator uses the inputs entered by the editor to create the Decision Support Software Definition Sets that are loaded into the customer's devices via the Deployment Manager. Includes consistency checking that performs a verification that all outputs and inputs are consistent across the Decision Support Definitions and Device Configuration Data that are defined for this device in the Device Definition Library.

Presentation Simulator provides a simulation of the Medical Devices user interface onto the Editors Platform that will appear on the various devices within the customers system. Customer may be able to simulate all of the inputs, defined in the Decision Support Definitions and visualize the response to those inputs created by the Decision Support Definitions.

Deployment Manager provides the capability of the customer to manage approvals/authorization/authentication of the Decision Support Definitions and works in conjunction with the Device Definition Library to authorize and track the deployment of new Decision Support Software Definition Sets.

Figure 5:
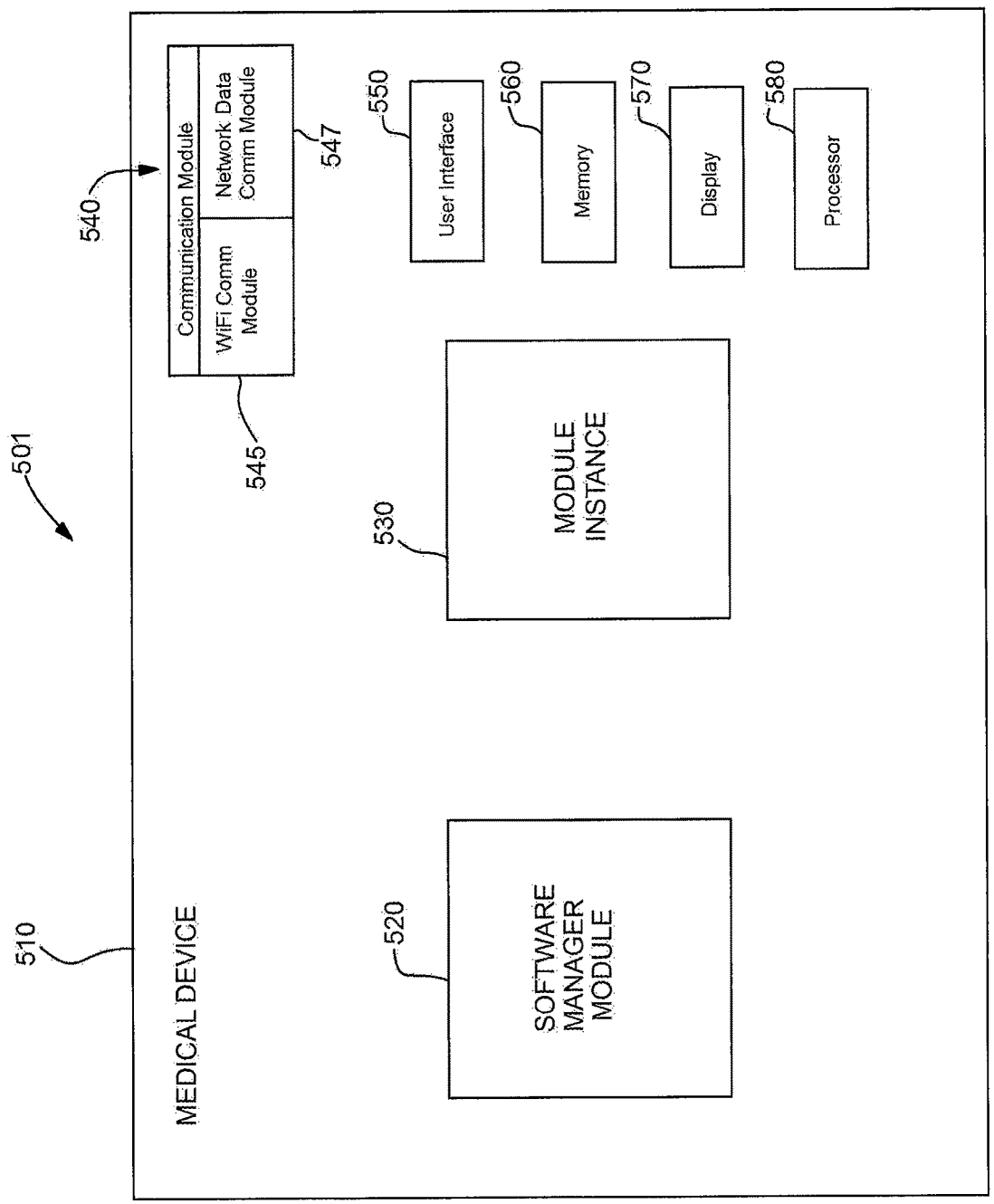
FIG. 5 illustrates a medical device including a computing architecture of this disclosure.

Turning now to FIG. 5, FIG. 5 illustrates a medical device 510 including a computing architecture of this disclosure comprising a memory 560, a processor 580 in communication with the memory, and an instance module 530 including an instance of a primary rules-based service configured to provide instruction events, the instance providing a primary processing thread of instruction events for coaching treatment of a patient. A software manager module 520 includes an artificial intelligence architecture. The artificial intelligence architecture is configured to provide an instance of a conditional rules-based service for providing instruction events. The instance of the artificial intelligence architecture provides a processing thread of instruction events for coaching treatment of a patient that is independent of the primary processing thread and is configured to trigger an action on the occurrence of a pre-defined set of input conditions.

The medical device of this disclosure illustratively further includes a communication module 540, a user interface 550, and a display 570.

Communication module 540 is hardware and software configured to transmit data to or from the medical device. Illustratively, the communication module is configured to transmit data from the medical device to an external utility. The external utility may be a computer, a laptop, a server, a mobile computing device, or other computing device. Alternatively, the utility module may transmit data from a utility to the medical device. The communication module may include a Wi-Fi communication module 545 configured to provide wireless communication. While illustratively configured for Wi-Fi, the communication module may employ one or more wireless communication implementations using any standard or using a non-standardized wireless implementation. The communication module may further include a Network data communication module 547 configured to provide for hardwire communication. The communication module is configured to provide bidirectional wired transmission of data from out of and to the medical device through the communication module.

Memory 560 can be any form of data storage. It may be at least one of random access memory (RAM) and/or read only memory (ROM). Information can be stored permanently until overwritten and/or stored temporarily for use while the unit is active.

Display 570 of the medical device may be a visual display capable of displaying data generated in or transmitted to the medical device. Displays for use with this disclosure may include an LCD screen, an e-paper display, or other bi-stable display, a CRT display or any other type of visual display.

User interface 550 may include a keypad. In an alternative illustrative embodiment, the user interface may be a touch screen keypad that is rendered on the display and which allows a user to enter data or to read data that is rendered on the display. In one embodiment the display is dedicated to providing touch screen keypad functionality. User interface may include a speaker, a microphone, manual buttons, or one or more other controls that allows a user to interact with the medical device.

The medical device may also include a power source (not shown). To enable portability of the medical device, power source typically includes a battery. Such a battery is typically implemented as a battery pack, which can be rechargeable or not. Sometimes, a combination is used, of rechargeable and non-rechargeable battery packs. Other embodiments of power source can include an AC power source.

The medical device of this disclosure may communicate with external utilities which together may provide a patient care system ("Patient Care System"). The medical device of this disclosure may also communicate with external utilities which together may provide a decision support system ("Decision Support System). For purposes of this disclosure, the term Decision Support System includes both a Patient Care System and a Decision Support System that is other than a Patient Care System. The external utilities that may be linked to the medical device through communication module may include a series of Medical Devices, such as monitors and defibrillators, and medical device viewers ("Medical Device Viewers"), such as personal computers, table computers, wall monitors, etc. that operate together to create an advance tool set for diagnosing and treating patients who are experiencing an emergent condition. The Decision Support System of this disclosure provides help to the clinical user in diagnosing patient conditions, determining appropriate treatment paths, and recording what treatment activities have occurred. Help is provided through a series of Smart Algorithms to help identify potential patient conditions, Messages/Reminders to inform the user to perform some task or action, a series of checklists helping the user follow a pre-defined treatment path, or the display of Reference Material or Calculators to help the user determine proper course of action or dosing.

The Decision Support System of this disclosure utilizes sets of conditional rules that are programmed to trigger specific actions by the system when certain shared communications are received. In one illustrative embodiment described in this disclosure the artificial architecture uses an Intelligent Agent architecture, in which each conditional rule is embodied as an Intelligent Agent. However, the disclosure and claims cover other embodiments that use a different implementation architecture, such as a rule engine, expert system, or other artificial intelligence architecture.

Intelligent Agents operate in conjunction with broader Software Managers (e.g., the software process) that control the operation of the Medical Devices that make up the system. In one illustrative embodiment, dozens, or hundreds of intelligent agents operate with one or more Software Manager. These Software Managers that work in conjunction with Intelligent Agents or other embodiments of conditional rules, include but are not limited to: an algorithm manager that monitors vitals known as Smart Vitals/Algorithm Manager, an algorithm manager that monitors a checklist known as a Checklist Manager, an algorithm manager that monitors an event known as an Event Viewer Manager, an algorithm manager that provides help known as a Help Manager, an algorithm manager that monitors an alarm known as an Alarm Manager, an algorithm manager that monitors readiness a medical device or other network resources or assets known as a Readiness/Asset Manager, an algorithm manager that monitors and generates reports known as a Report Manager, and an algorithm manager that monitors a patient case known as a Patient Case Review Manager.

These agents may run independently of the main processing threads within the Software Manager and trigger action by the Software Manager when a pre-defined set of input conditions are true. These Intelligent Agents may be customizable by an administrator such as a medical director ("Medical Director"), allowing the customer to decide what agents they want running, and what response they want from the Decision Support System when the Intelligent Agent input condition is fully met. This allows an administrator, like a Medical Director, to select the number of Decision Support Definitions they want operating in their system and to tailor the specific user interface response when the Intelligent Agent is triggered.

Figure 6F:
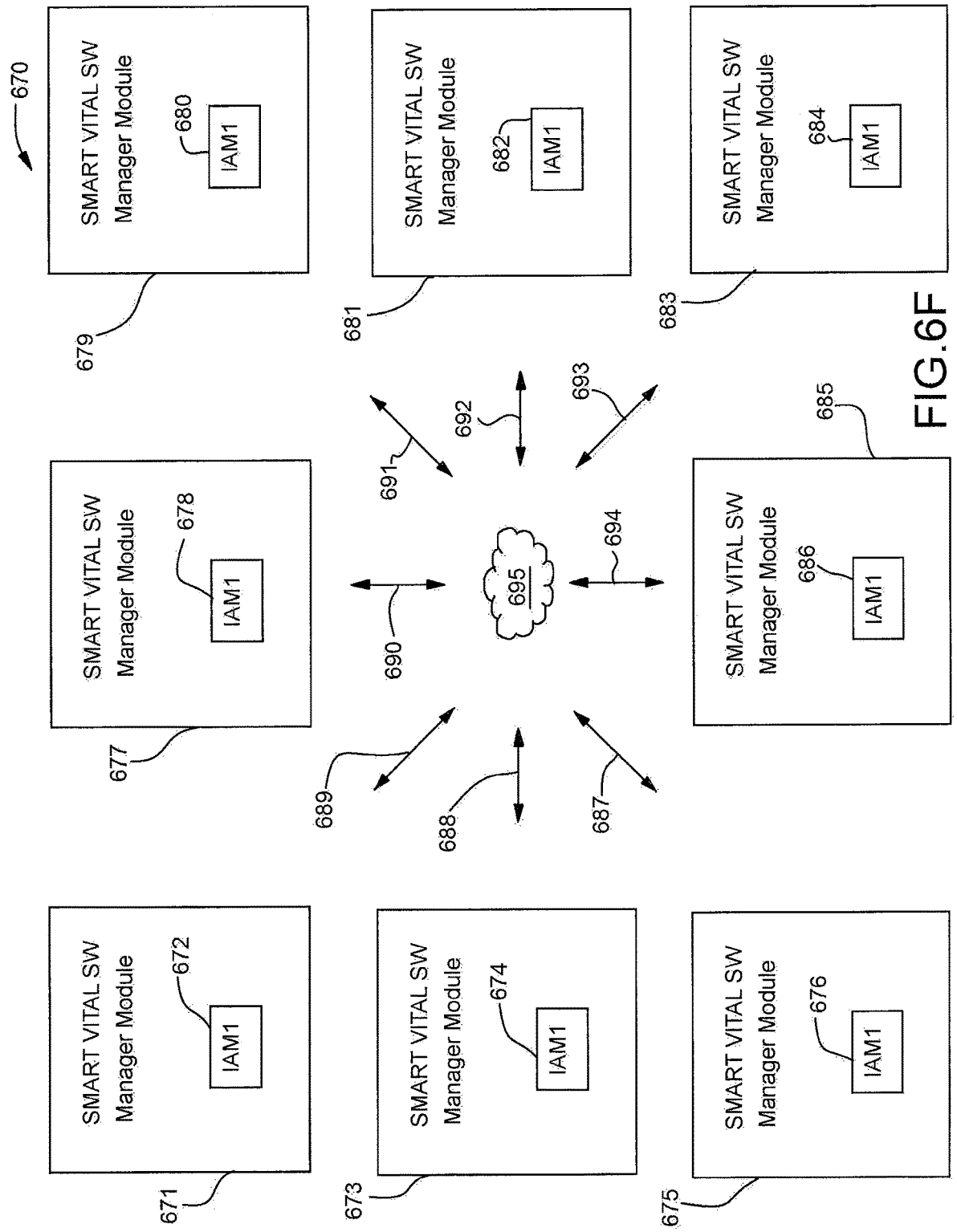

FIGS. 6A-6F show illustrative embodiments of a medical device including a computing architecture of this disclosure. FIG. 6A shows a medical device 610 including a Software Manager Module 612 which includes an architecture involving Intelligent Agents shown in FIG. 6A as Intelligent Agent Module 614. Illustratively, the SW Manager Module also includes the Software Manager as that term has been previously defined. The Intelligent Agent executes concurrently with the Software Managers that control the presentation to the users.

FIG. 6B shows a medical device 620 including a Software Manager Module 622 including an architecture involving an Expert System shown in FIG. 6B as Expert System Module 624. FIG. 6C shows a medical device 630 including a Software Manager Module 632 including an architecture involving a Rule Engine shown in FIG. 6C as Rule Engine Module 614.

FIG. 6D shows a medical device 640 in which a Software Manager Module 642 includes a plurality of Intelligent Agents including Intelligent Agent 642 and Intelligent Agent 644. In FIG. 6E, two medical devices 652, 656, each including a Software Manager Module shown in FIG. 6E as 653, 654, respectively, and each including an Intelligent Agent shown as Intelligent Agent IAM1 654, and Intelligent Agent IAM2 657 communicate between themselves over a communication link 655. In FIG. 6D, each medical device illustratively serves as an external utility to the other.

FIG. 6F shows a network 670 of medical devices 671, 673, 675, 677, 679, 681, 683, and 685 distributed across the network. Each medical device is provided with a Software Manager Module including an Intelligent Agent and each medical device may illustratively be in communication with one or more other medical device of the distributed network. As explained later, a network may be provided with other external utility devices to make the system of this disclosure a more powerful decision support system.

Hence, this disclosure provides a computational collaborative decision support system in which a primary decision support system is empowered with intelligent agents or other artificial intelligence constructs to help a decision-making caregiver make effective treatment decisions or a decision-making team collaborate with each other better to make effective treatment decisions.

The collaborative support system of this disclosure is more complex than conventional individual decision support systems because the process involves interactions between the decision-making artificial intelligence architecture, such as agents, and the caregiver and/or team of caregivers that may require complex software. The tradeoff is a more powerful decision support system because the decision-making artificial intelligence architecture, such as agents, of the collaborative decision support system of this disclosure may leverage information processing capabilities of others in providing a caregiver or team of caregivers with coaching. For example, the collaborative decision support system may leverage processing capabilities of information gathering by the medical device or other resources in a network. The collaborative decision support system may leverage filtering for a particular condition, such as sepsis, one of the detailed examples explained below of using the medical device of this disclosure. The collaborative decision support system may integrate data and processes for use by the caregiver and/or team of caregivers in treatment of a patient. The collaborative decision support system of this disclosure enables better quality decisions to be made such as in terms of timeliness or correctness. The collaborative decision support system of this disclosure provides for collaborative situation awareness based upon types of decision-making tasks.

The collaborative decision support system of this disclosure makes decisions on what to do next. Each decision-making task of the collaborative decision support system has certain knowledge requirements. For example, in a scenario involving treatment of a patient, a caregiver needs to monitor the patient, and to decide how to respond to the conditions of the patient. For this purpose, the collaborative decision support system provides an instance of a primary rules-based service to coach the caregiver or team of caregivers. More specifically, the instance of a primary rules-based service provides a primary processing thread of instruction events for coaching treatment of a patient.

Illustratively, the decision-making provided by the primary thread of instruction events provides coaching based upon measured patient parameters such as temperature, heart rate, etc. that is translated into cues internal to the instance of a primary rules-based service regarding how threatening is the condition of the patient and what is the recommended protocol to follow for treatment of that condition. The rules of the instance of a primary rules-based service specify how to combine cue values to determine the level of threat and the recommended protocol to follow. The instance of a primary rules-based service generates the recommended protocol which may include one or more actions for a caregiver to perform. The instance of a primary rules-based service may be interactive with the caregiver. For example, the instance of a primary rules-based service may prompt the caregiver for feedback following performance of one or more actions which may then be factored into the decision tree being processed by the instance of a primary rules-based service in determining the next action.

Decision-making in treating a patient is typically connected with treatment hierarchies. A higher-level decision-making task is based upon a condition or set of conditions that may indicate a higher threat to the patient. A lower-level decision making task is based upon a condition or set of conditions that may indicate a lower threat to the patient. The collaborative decision support system of this disclosure may organize threats hierarchically according to decision types.

Figure 7:
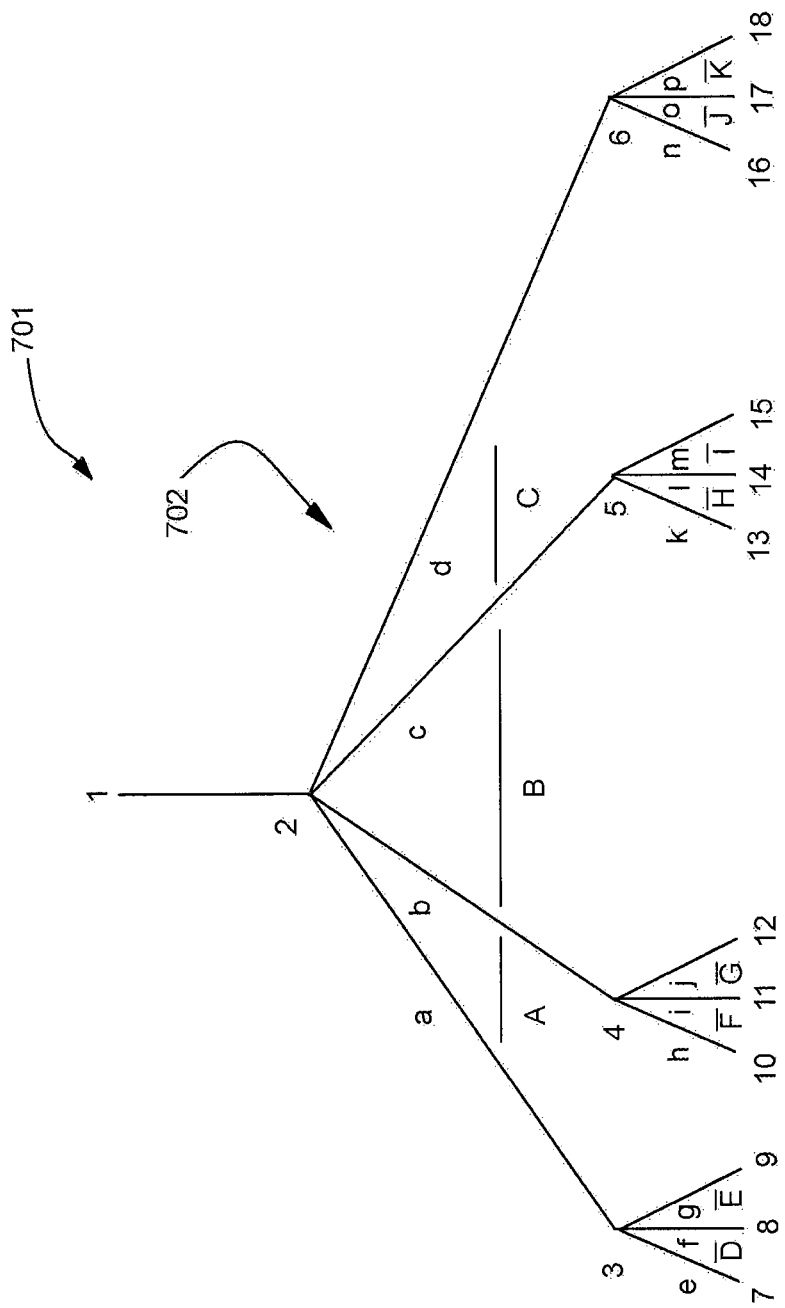
FIG. 7 is an illustrative decision tree made possible by the decision support system of this disclosure.

As discussed in connection with FIG. 4, conventional decision support systems typically commence by determining the threat of a patient and then executing a treatment protocol for treating that threat. FIG. 7 shows a decision tree 701 for an illustrative protocol 702 of this disclosure. The protocol defines a decision tree of events or rules 1-18. Rule 1 may be a selection of the protocol by the user. Each internal (non-leaf) node or rule 2-6 denotes a test on an attribute. Each branch or expected outcome a-p represents the outcome of a test provided by the rules 2-6. Each leaf (or terminal) node 7-18 holds a class label which is the label for the treatment. By way of example, rule 2 provides 4 branches or expected outcomes which might be a protocol treatment for treating infection a, a protocol treatment for treating sepsis b, a protocol treatment for treating trauma c, and a protocol treatment for treating sirs d. Each of branches a-d lead to new rules 3-6, respectively, which in turn lead to branches or expected outcomes which might be protocol treatments e-p. Nodes 7-18 represent the end of the protocol which is the ultimate expected outcome and the label for the treatment. The foregoing decision tree may be referred to as the "branching decision tree" and would be illustratively executed by the instance of a primary rules-based service of this disclosure. The artificial intelligence architecture, such as Intelligent Agents, of this disclosure allow for the path navigated through the decision to be changed based on treatment hierarchies. Hence, the artificial intelligence architecture, such as Intelligent Agents, of this disclosure allows navigation through the decision tree to advantageously change from one branch to another branch as illustrated in FIG. 7 by navigational changes A-K.

The artificial intelligence architecture of this disclosure is configured to provide an instance of a conditional rules-based service for providing instruction events. The instance of a conditional rules-based service provides a processing thread of instruction events for coaching treatment of a patient that is independent of the primary processing thread and is configured to trigger an action on the occurrence of a pre-defined set of input conditions. The instance of a conditional rules-based service illustratively continually monitors one or more conditions in the background and triggers an action that may override the action of the primary processing thread when it involves higher-level decision-making task. As explained in detail later, the onset of sepsis may be a higher-level decision-making task than a task involving treatment of a wound, for example. The primary processing thread may be instructing the caregiver on treating the wound while the processing thread provided by the artificial intelligence architecture may be monitoring for sepsis. On the onset of sepsis, the processing thread of sepsis treatment steps of the artificial intelligence architecture may override the instructions being provided by the primary processing thread of wound caring actions.

In conventional decision support systems, a decision task may be selected by a pre-specified step in a plan. Alternatively, the decision task could be requested from a caregiver or a team of caregivers. Likewise, in the artificial intelligence architecture of this disclosure, a decision task may be selected by a pre-specified step in by a request from a caregiver or a team of caregivers. Advantageously, in the artificial intelligence architecture of this disclosure, the decision task may also be dynamically identified by an agent itself. In this way, decision-making and information are tightly coupled at multiple levels. In other words information from the artificial intelligence architecture of this disclosure is integrated into the decision tree and decision results.

The artificial intelligence architecture of this disclosure may be used to coach a caregiver performing a treatment, such as in the field or in a hospital setting. The artificial intelligence architecture of this disclosure may also be used to support teams where knowledge and expertise are distributed across a network. For instance, members of a hospital team may have different information, knowledge, and/or expertise access than a caregiver performing a treatment such as due to their expertise, roles and responsibility in the team. The team members may make decisions at different levels relative to their information, knowledge, and/or expertise that the collaborative decision support system of this disclosure may incorporate into the coaching provided by the disclosed decision support system. For example, the artificial intelligence architecture of this disclosure information may respond to information provided by one or more members of the team with a higher-level decision-making task and so coach the caregiver administering the treatment. Advantageously, an agent of this disclosure may be involved in individual or multiple decision tasks. In either case the agent may have relations. Hence, the agents of this disclosure may be configured to effectively manage multiple attentions, that is to say, processes. The design of attention management by an agent of this disclosure is a matter of agent design architecture.

Figure 8:
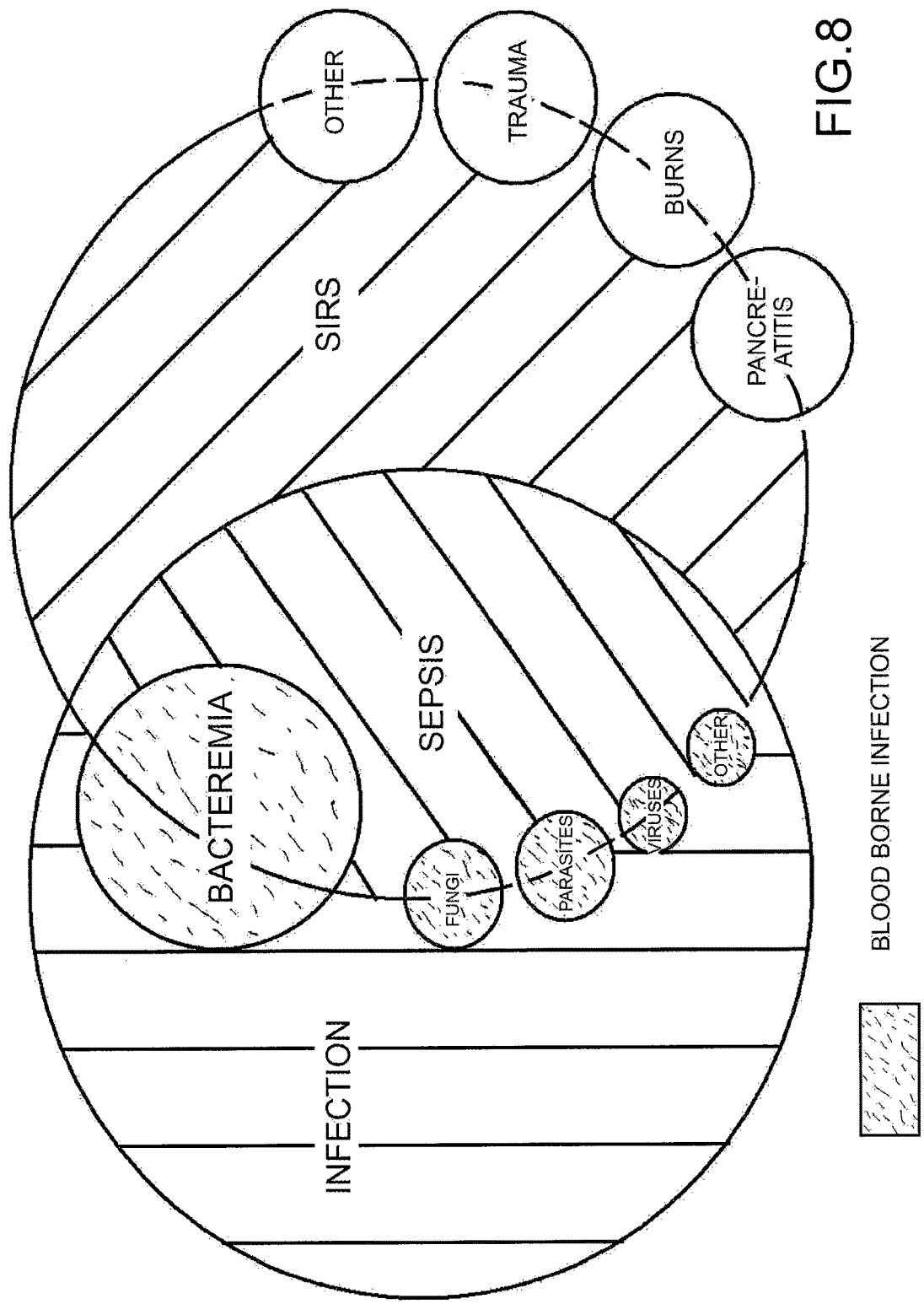
FIG. 8 is a prior art depiction showing some contributors of sepsis.

We now turn to how to the artificial intelligence architecture of this disclosure may represent the threat. We illustrate one representation for the determination of sepsis. The onset or existence of sepsis is an increasingly common cause of morbidity and mortality, particularly in elderly, immunocompromised, and critically ill patients. FIG. 8 shows some contributors of sepsis which may include infection, bacterium, fungeria, and systemic inflammatory response syndrome (SIRS) which may arise from noninfectious pathological causes including pancreatitis ischemia, multiple trauma and tissue injury, hemmorrhagic shock, immune-mediated organ injury, and the exogenous administration of such putative mediators of the inflammatory process as tumor necrosis factor and other cytokines. Early goal-directed therapy is beneficial to patients with sepsis. The artificial intelligence architecture of this disclosure may be used to represent this sepsis threat.

Figure 9:
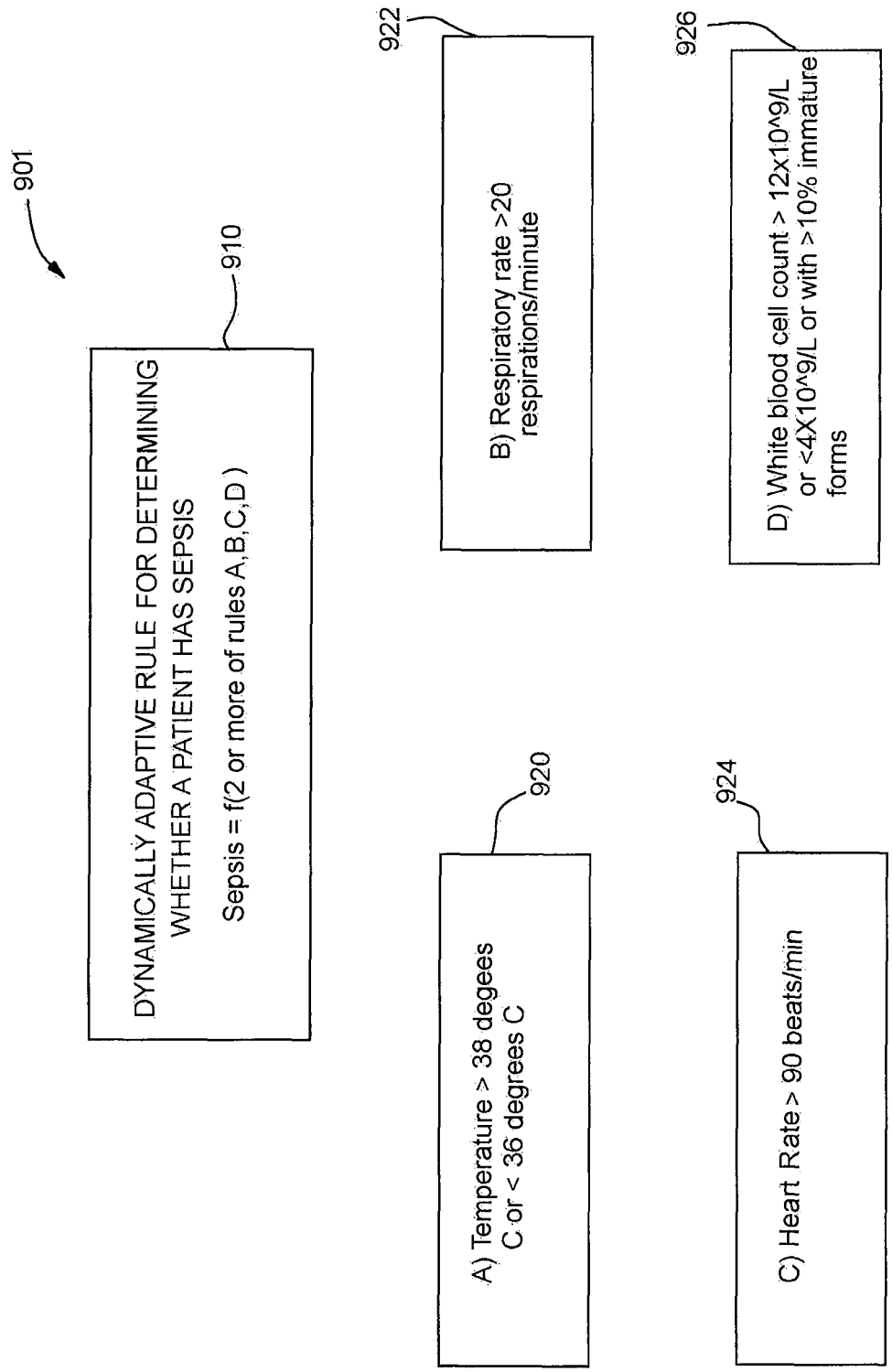
FIG. 9 shows a dynamically adaptive rule for determining whether a patient has sepsis using the artificial intelligence architecture of this disclosure.
Figure 10:
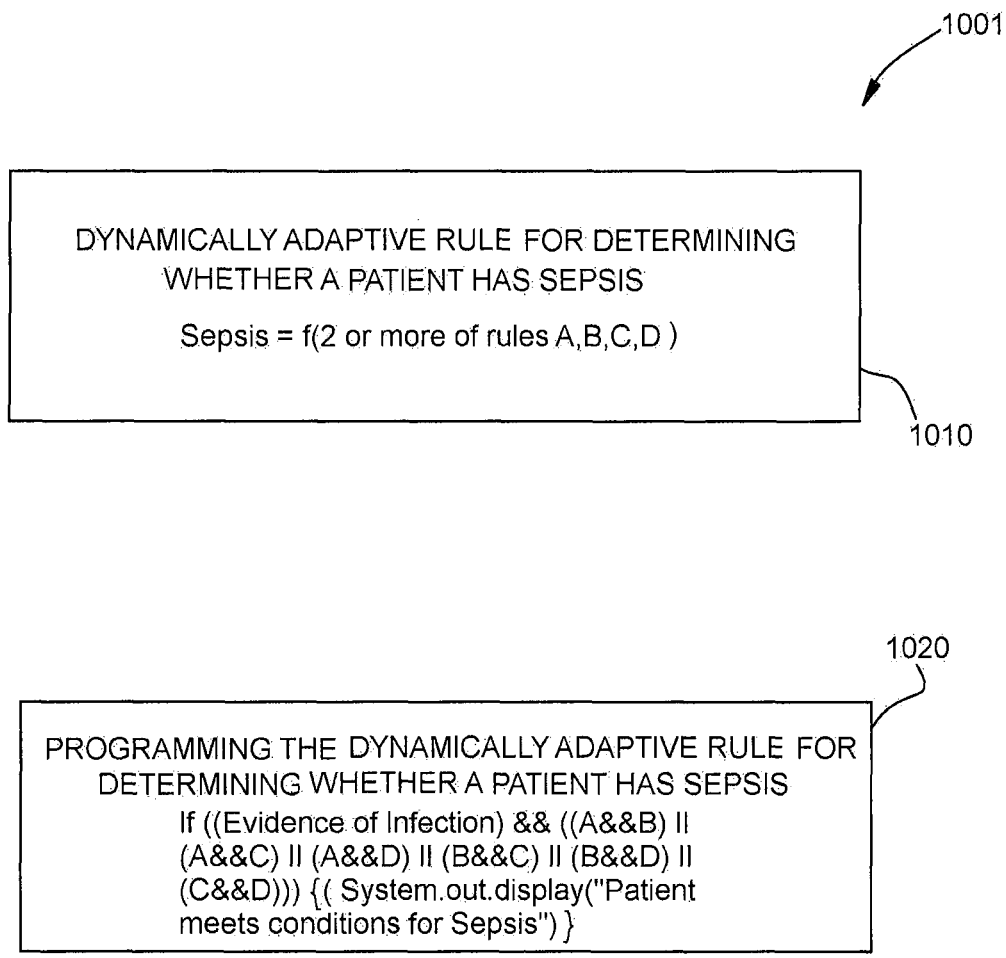
FIG. 10 shows an illustrative logical expression of the rule detailed in FIG. 9.

According to this disclosure, each threat may be characterized as a number of parts. FIGS. 9 and 10 show an illustrative way in which a threat of sepsis may be characterized for use with this disclosure. FIG. 9 shows an illustrative model 901 for use by an Intelligent Agent in the detection of sepsis. According to this model, the existence of sepsis is detected on the presence of "2 or more" of the following rules with definitive evidence of infection:

Temperature>38 degrees C. or <36 degrees C.
Heart Rate>90 beats/min
Respiratory rate>20 respirations/minute
White Blood cell count>$12\times10^9$/L or <$4\times10^9$/L or with >10% immature forms As shown in FIG. 9, the sepsis threat illustratively has three parts in this example: cues, goal, and course of action. The cue are the rules on individual patient parameters. The rules are shown in FIG. 9 as rules 920, 922, 924, and 926 previously explained. The goal is the determination that the condition of sepsis exists. The threat analysis makes that determination in the illustrative example based on the existence of true conditions in two or more of the indicated rules. The course of action is a plan or protocol for treatment of the sepsis once the existence of sepsis has been determined. As explained in this disclosure, on the existence of the condition of sepsis, by the artificial intelligence architecture of this disclosure, illustratively an Intelligent Agent, an alert and instructions may be imposed upon the medical device to make the caregiver aware of the sepsis condition and provide coaching to the caregiver for treating the sepsis by way of a treatment protocol.

FIG. 10 shows one illustrative correlation 1001 in which the four parameters shown in FIG. 9 may be correlated to each other to express the output rule 910 to have one of the two permissible outputs previously explained. The rule is expressed again in a statement of the rule 1010 which states that:

Sepsis=f(2 or more rules A, B, C, D)

A logical expression 1020 of this output rule 910 may illustratively be provided using Boolean logic to express the output rule 910 in the following form:

If ((Evidence of Infection) && ((A&&B) 11 (A&&C) 11 (A&&D) 11 (B&&C) 11 (B&&D) 11 (C&&D)))

For an Intelligent Agent programed with this rule, logical expression 1020 provides an output of logical 1 if true or 0 if not true. If the output is true, the Intelligent Agent has detected sepsis. In the illustrative example, the Intelligent Agent alerts the caregiver by an alert event. For example, the Intelligent Agent may issue a device alert in the form of a display that "Patient meets conditions for Sepsis" as indicated by the following instruction in the protocol.

{System.out.display ("Patient meets conditions for Sepsis");}

In this example, the artificial intelligence architecture of the software manager module is providing an instance of a conditional rules-based service for providing instruction events. In this case, the instance provided a processing thread of instruction events for coaching treatment of a patient for patient. This instance was operating independently of the primary processing thread and it triggered an action, namely, the alert, on the occurrence of a pre-defined set of input conditions indicative of sepsis.

As indicated, the cue may be the rules on individual patient parameters that are indicative of the medical condition such as sepsis. The cue may also be some elementary data. More particularly, the term "cue" may be an agent's internal representation of the decision situation. The cues may be higher-level abstractions of some elementary data.

The cues may also be some synthesis of lower-level information. In the illustrative example of FIG. 9, the cue is a higher-level abstraction of some elementary data. The abstraction takes the form of rules rather than the elementary data in this example. In another illustrative example, the cue may be the root of two or more tree-like information-dependence structures. The root may describe the way in which the cue is abstracted from low-level information. The example in FIG. 9 illustrates the rule as the root of four tree-like information dependency structures.

FIG. 11 illustrates another way in which the threat may be represented. As shown in FIG. 11, the threat illustratively has four parts: cues, goals, course of actions, and expectancies. The cue are the rules on individual patient parameters. The goal is the determination of sepsis. The threat analysis makes determinations in the illustrative example based on the existence of true conditions in one or more of the rules. The course of action is a plan for treatment on sepsis once the existence of sepsis has been determined. The expectancies are the expected outcomes.

More specifically, a prior art protocol for the management of sepsis comprises a set of rules 1120 that define caregiver treatments 1110 and expected treatment outcomes 1130. The treatments 1110 may include fluid replacement, control of blood pressure, tissue perfusion, early treatment with antibiotics, administration of steroids for adrenal insufficiency, control of blood glucose levels, protective lung ventilation, and administration of activated protein C.

The set of rules 1120 comprise individual rules 1121-1128. Rule 1122, for example, is a rule for the treatment control of blood pressure 1140 and provides for a test on an attribute referred to as the mean arterial blood pressure (MAP), an attribute well known in the art. As shown in FIG. 11, if the outcome of the MAP test is equal or greater than 65 mm Hg after fluid replacement, then the branch or expected outcome 630 of that test might be to continue monitoring MAP. If, however, the outcome of the MAP test is less than 65 mm Hg after fluid replacement, then the branch or outcome of that test might be to adjust dosage of norepinephrine. The leaf (or terminal) node in this case might hold a class label which is the treatment and is denoted as the control of blood. For an Intelligent Agent programed with these rules, logical expression 1120 provides an output of logical 1 if true or O if not true. If the output is true, the Intelligent Agent has detected the indicated condition. In the illustrative example, the Intelligent Agent alerts the caregiver by an alert event. For example, if rule 1121 were true, the Intelligent Agent may issue a device alert in the form of a display that "Patient meets conditions for Fluid Replacement" as indicated by the following instruction in the protocol generated by the Intelligent Agent.

{System.out.display("Patient meets conditions for Fluid Replacement");}

As previously described, the collaborative decision support system of this disclosure places no restriction on the sources of decision tasks. It could be a pre-specified step in a plan, could be a request from a human partner or other teammates, or could be dynamically identified by an agent itself. Hence, the decision task may be selected by a pre-specified step in a plan. The decision task may be requested from a caregiver or a team of caregivers. Advantageously, in the artificial intelligence architecture of this disclosure, the decision task may be dynamically identified by an agent itself.

To initialize the process, from the current situation, the collaborative decision support system determines the collection data that are potentially relevant to the task. In one illustrative embodiment, the caregiver or any one of a team of caregivers select the decision task that provides the protocol for treatment. The collaborative decision support system explores the decision space hierarchy to pick one that is applicable to the decision task. A decision process is chosen and fixed as the primary processing thread of instruction events for coaching treatment of a patient based on a primary rules-based service. An instance of a primary rules-based service provides a primary processing thread of instruction events for coaching treatment of a patient. In the background, the artificial intelligence architecture provides an instance of a conditional rules-based service for providing instruction events. The instance provides a processing thread of instruction events for coaching treatment of a patient that is independent of the primary processing thread and is configured to trigger an action on the occurrence of a pre-defined set of input conditions.

If the pre-set defined set of input conditions does not occur, the collaborative decision support system continues processing the primary thread of instruction events for coaching treat of a patient based on a primary rules-based service. However, if the pre-set defined set of input conditions occurs, the instance of a conditional rules-based service of the artificial intelligence architecture of the collaborative decision support system provides instruction events. The instance provides a processing thread of instruction events for coaching treatment of a patient that is independent of the primary processing thread and is configured to trigger an action on the occurrence of a pre-defined set of input conditions.

An intelligent agent may trigger an action on the medical device, such as an alert, or rendering of an instruction of a treatment protocol on a display of the medical device. For instance, referring again to FIG. 11, the task of tissue perfusion is a treatment that involves several sub-tasks. One is the assessment for evidence of adequate tissue perfusion such as heart rate, respirations, urine output, mentation. This sub-task may be assigned to a first intelligent agent. Another sub-task is the monitoring of Scv02 which may be assigned to a second intelligent agent. Another sub-task is the monitoring of hematocrit which may be assigned to a third intelligent agent. In this example, three intelligent agents are monitoring for different conditions. The first intelligent agent may output its assessment as data rendered on a display of the medical device. The second intelligent agent may also output its assessment as data rendered on a display of the medical device. The third intelligent agent may create an alert on the occurrence of the condition that it is monitoring (i.e., Scv02 is less than 70% after CVP and MAP corrected. The fourth intelligent agent may output its assessment as data rendered on a display of the medical device.

The intelligent agent may also trigger an action in another agent. For instance, the task of control of blood pressure involves monitoring mean arterial pressure, known as MAP, involves the sub-tasks of monitoring MAP and adjusting dosage of norepinephrine if MAP<65 mm Hg after fluid replacement. The task of control of blood pressure may be assigned to a first agent. Alternatively, the sub-task of monitoring MAP may be assigned to one agent and the task of control of blood pressure may be assigned to a second agent. In this example, the output from the first agent may be applied as an input to the second agent. When the MAP drops below 65 mm Hg, this input from the first agent causes the second agent to generate an alert to the caregiver to adjust the dosage of norepinephrine.

To initialize the collaborative decision support system in another illustrative embodiment, the caregiver, any one of a team of caregivers or the artificial intelligence architecture of this disclosure may select the decision task that provides the protocol for treatment. After selection, the collaborative decision support system proceeds as previously described. This allows for the artificial intelligence architecture of this disclosure to override a selection of the caregiver or any one of a team of caregivers.

In the foregoing and other examples, the primary processing thread and the processing threads of each artificial intelligence architecture, such as intelligent agents, are executing effectively contemporaneously; albeit illustratively one or a subset of the processing threads may be effectively triggering an action on the medical device at one point in time. These threads may be organized within a decision space in a hierarchical fashion such that the higher-priority threads have priority over threads of lower priority. For example, a processing thread of an artificial intelligence architecture, such as intelligent agents, associated with sepsis, may have a higher priority than a primary processing thread currently being executed in which event the higher priority processing thread associated with sepsis will execute to provide actions to the caregiver or team of caregivers instead of the actions being provided by the primary processing thread once the processing thread of the artificial intelligence architecture has determined the existence of sepsis. If there are two processing threads associated with one or more artificial architectures (i.e., which may come from the same or different agents, expert systems, rule engine modules, or other artificial architectures) that have a higher priority than the primary processing thread currently being executed, then as between the two threads, the one with the higher priority may execute first to provide actions to the caregiver. After the higher priority thread has executed the actions called for by that instance, the collaborative decision support system may determine which processing thread now has the higher priority.

In one illustrative embodiment, a caregiver or a team of caregivers may over-ride any thread that is being executed or manually select another thread to execute from the decision space hierarchy in which the may be organized. The agent of this disclosure may derive information requirements pertaining to a current decision task from the cues under its consideration. A plurality of agents in a team illustratively play different roles when investigating a situation. For example, one agent may play the role of monitoring for sepsis while another agent may play another role. A plurality of agents distributed across a network may play the same or different roles. For instance, the agent for monitoring sepsis may be distributed across the network in a plurality of medical devices in a network. An agent for monitoring assets may be centrally located in the network. Hence, a plurality of agents distributed across the network are seen to play the same role than one or more agents performing different roles across the network.

In addition, the agents while trying to synthesize the available information into appropriate cues, may ask for help from some potential information providers. For instance, an agent may ask a caregiver or team of caregivers for certain information. On receiving that information from teammates, the agents may synthesize the new acquired information to develop better situation awareness. The agents may also learn new information-dependency trees from a caregiver or team of caregivers, and revise experiences in its experience knowledge database to incorporate additional cues. The agents may also revise experiences in its experience knowledge database based on new information from other agents.

Network resources, including experts, who have the experiences relevant to a current task may tell the agents about the information relevant to the cues that need to be considered. Since agents may have different experience knowledge databases and information-dependence structures, the agents and network resource can inform other agents and network resources about the cues that have been synthesized in ways beyond the existing expertise of the agent and the network resource. In addition, the agent's network resources may share experiences by informing the cues and other resources of important information. An agent that has no experience pertaining to a current task may help another agent upon being requested of certain information. For example, an agent may reply to another agent with information that is synthesized in a way different from the structure being considered by the other agent.

An important part of an investigation process is evolving recognitions. The anytime instances of this disclosure allow an agent to trigger an output at any point of the investigation process, so long as the agent has attained a satisfactory level of awareness of the current situation.

The agents of this disclosure may be configured to trigger an output of a current situation based upon a past experiences that most matches the current situation. For example, an agent may include a set of past experiences for sepsis such as sepsis conditions according to age, sex, race, etc. The agent may execute a process thread based upon a match of the current situation with one of these past experiences. If the situation faced by the agent is an unfamiliar situation, the task of the agent may be more than cue-driven information investigation. The agent may need to identify a collection of cues which the agent may synthesize using prescribed rules.

For adaptive learning according to this disclosure, an administrator may consider both the positive and negative evidences collected in one or more artificial intelligence architecture, such as intelligent agents, and to reconcile conflicting evidences reported by different artificial intelligence architectures, as well as the caregiver and/or caregiver team members, if any. Certain human-adjustable thresholds can be used to judge whether a rule, hypothesis for the situation, or the like are applicable to the current situation. If not, the administrator may reconfigure the artificial intelligence architecture to generate additional evidences which may be used to explore another rule, hypothesis for the situation, or the like until the administrator finds an acceptable one. Once the administrator proves the rule, hypothesis for the situation, or the like works, the rule, hypothesis for the situation, or the like will be stored as a valid experience for dealing with future similar situations.

As part of this disclosure, the administrator may synthesize experiences of two or more past experiences to deal with an unusual situation. Synthesis may be based on experiences from one or more artificial intelligence architecture, such as intelligent agents, and the components of a synthesized experience may typically involve the coupling of the corresponding parts of the input experiences.

After an artificial intelligence architecture, such as intelligent agents makes a recognition, it will illustratively continuously monitor the associated expectancies until the completion of the selected course of actions. This expectancy monitoring is important to adaptive decision-making. An artificial intelligence architecture, such as intelligent agents, can subscribe information relevant to the expectancies that need to be continuously monitored. The information subscribed may include patient parameter data. It may also include data from the caregiver, caregiver team, and/or other resources to take full advantage of the team's distributed cognition. In this way, the artificial intelligence architecture, such as intelligent agents, may trigger the appropriate task when the situation arises and terminate the actions that may have resulted from a wrong recognition at the earliest opportunity.

The artificial intelligence architecture, such as intelligent agents, may use expectancies to initiate complete new decisions. For example, if the expectancy is that sepsis exists on the occurrence of a predefined set of conditions, such as explained above, the expectancy serves as a gate-condition for the artificial intelligence architecture, such as intelligent agents, to keep following the current recognition. In addition, the artificial intelligence architecture, such as intelligent agents, may use expectancies to refine a decision. Illustratively, the artificial intelligence architecture, such as intelligent agents, may leverage some structures within the active experience knowledge database. If the artificial intelligence architecture monitoring an expectancy, such as sepsis, has detected the expectancy, but in fact the condition of sepsis does not exist in the patient contrary to the expectation, this invalidation of the expectancy may indicate that the once workable recognition is no longer applicable to the changing situation.

If the artificial intelligence architecture, such as intelligent agents, has already executed part of the selected course of actions, those actions may still make sense since the error in the expectancy was not known at the commencement of the course of action. However, the artificial intelligence architecture, such as intelligent agents, may make adjustments to the expectancy. The adjustments may be made on the fly by the caregiver and/or team of caregivers or other resources. For instance, if the expectancy is dependent on the temperature of a patient, the temperature may be a variable that a trained medical expert may remotely or at the site adjust in a particular situation; thereby adapting the expectance of the artificial intelligence architecture, such as intelligent agents, on the fly. An administrator may also make adjustments to the expectancy, also on the fly or after the fact. In either case, the adapted expectancy of the artificial intelligence architecture, such as intelligent agents, can be used for further recognition. If the adaption occurred in real time, the adapted expectancy enables the artificial intelligence architecture, such as intelligent agents, to start another round of recognition, using the refined experience to develop a better solution.

Figure 12:
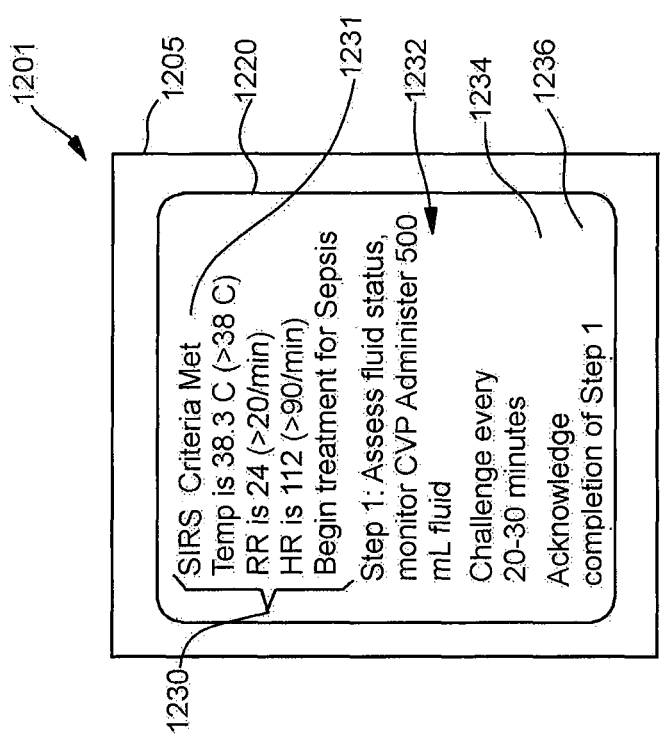

FIG. 12 shows an illustrative embodiment 1201 of a device alert 1220 that the medical device may provide to a caregiver on detection by the Decision Support system of this disclosure of a condition known as systemic inflammatory response syndrome, otherwise known as SIRS. The device alert 1220 is one or more pieces of data about the condition of the patient rendered on a display 1205 of a device (not shown). The device is illustratively a smart phone; but may be any other mobile device including a laptop, a notebook, a PDA, or any other mobile computing device. The device may also be a non-mobile device like a personal computer, a monitor, or any other computing device. The display 1205 may be any display provided by the device for rendering the device alert. It will be appreciated that the device may communicate the device alert by other than visual rendering. For example, device may include a loudspeaker for communicating an alert to the caregiver as an audible. Any user interface configured for communicating an alert to the caregiver is contemplated by this disclosure.

The device alert 1220 illustratively includes alert information 1230 alerting the caregiver of the existence of a disturbance. The alert data may include data that conditions 1231 have been met, particular data 1232 on events that have triggered the condition, and or one or more instruction data 1234 for the caregiver to follow in administering a treatment to correct the condition. FIG. 12 shows two instructions. The first instruction is step 1 which is "assess fluid status, monitor CVP, administer 500-mil fluid every 20-30 minutes." The second instruction is an "acknowledge completion of step 1." The user may acknowledge the completion of step 1 by manual activation of a button on the medical device. If the display 1205 is a touch screen, the "acknowledge" may be an active button which the caregiver may activate to signal the medical device that step 1 is complete. On completion of step 1, the cascade control system of this disclosure may display another instruction as step 2 and receive an acknowledgment from the caregiver on completion of that step of the treatment; and so on.

In this example, as previously explained, the Intelligent Agent is feeding these instructions for treatment of SIRS for rendering on the display in response to the Intelligent Agent having detected the onset or existence of SIRS. The instructions that the Intelligent Agent may be streaming to the caregiver may illustratively include those detailed in FIG. 11 as those conditions may be been detected by the Intelligent Agent which have been previously explained and displayed on device alert 1220 shown in FIG. 12. In this regard, instruction 1234 displayed in FIG. 12 will be recognized as rules 920, 922, and 924 in FIG. 9. As a next instruction for display on device alert 1220, the device alert 1220 may display the instruction associated with rule 1122 in FIG. 11 for the controlling of blood pressure. By providing one or more instruction on device alert 1220, the device alert 1220 may navigate the caregiver through the instructions that are generated from rules 1121 through 1128 shown in FIG. 11 for the treatment of sepsis. As previously explained, while these instructions are being fed and displayed to a caregiver in a particular order for action, the artificial intelligence architecture of this disclosure is continually monitoring the outcomes of each other rule of the protocol so that should any violation of any of these rules be detected while an outcome from another rule is being fed and displayed to the caregiver, the processing thread of the agent tasked with monitoring the violated rule may issue a correction for that error.

The instruction associated with rule 1121 shown in FIG. 11 further illustrates the task management function of the Intelligent Agent, which task management function may occur as a background or a foreground application. Rule 1121 calls for a challenge to the caregiver every 20-30 minutes. The artificial intelligence architecture, like Intelligent Agents, of this disclosure may manage this task by calendaring the event on an internal calendar and prompting the caregiver at the expiration of the 20 minutes. The agents may work with the Software Managers to control the information that is provided to the user. In this way, not only does the disclosed decision support system provide instructions to a caregiver on steps to take through a branch decision tree for a treatment, but the disclosed decision support system may manage all tasks that may be associated with instructions including calendaring, prioritizing, managing those tasks, and issuing instructions to the caregiver when it comes time for that task to be performed by the caregiver.

Figure 13:
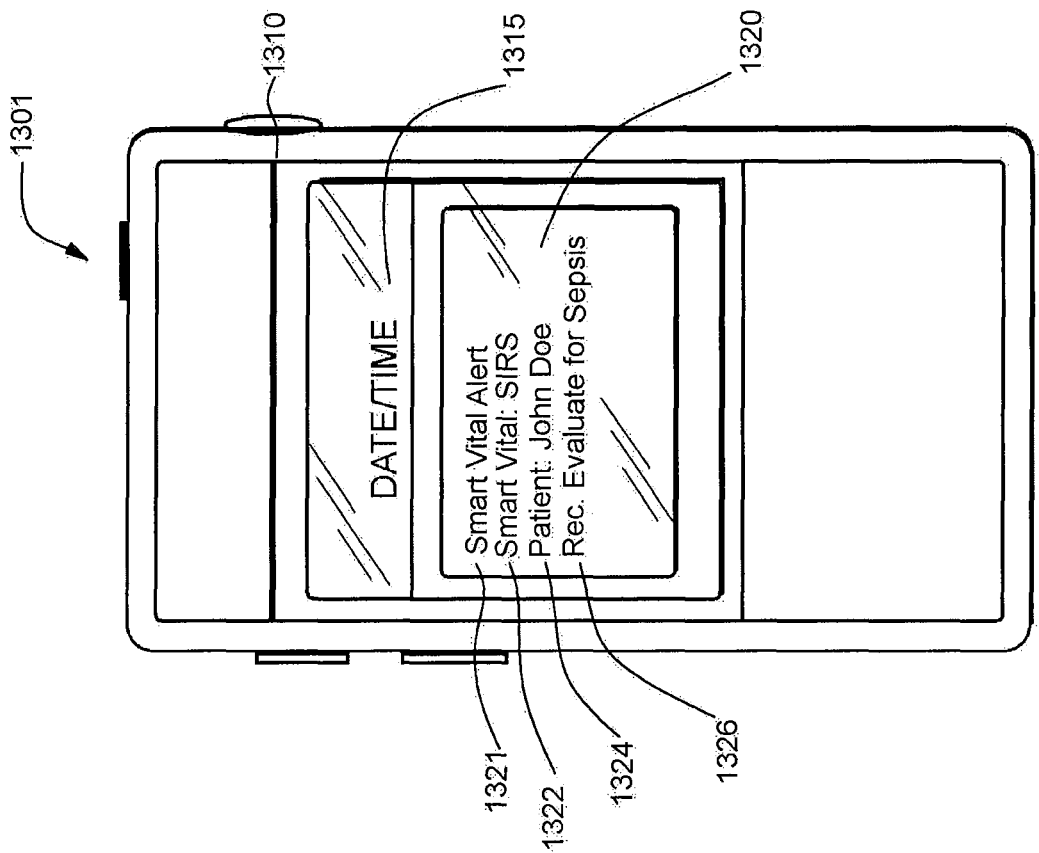
FIG. 12 and FIG. 13 show an illustrative device alert from the decision support system of this disclosure.

FIG. 13 shows an alternative embodiment 1301 of a Decision Support system of this disclosure. The embodiment 1301 includes a device 1310, a display 1315, and a device alert 1315 which includes an alert 1321 for the purpose of prompting the caregiver about the existence of a condition, data 1321 on the condition itself; in this case the onset or existence of SIRS in a patient, data 1324 on the identity of the patient, and an instruction 1326 instructing the caregiver to evaluate for sepsis. In this illustrative embodiment, the disclosed control system merely prompts the caregiver to evaluate for sepsis; leaving it to the caregiver to determine and administer the steps for the treatment of sepsis. In this case, the instance of a primary rules-based service may be put into a pause mode, suspending further navigation through the branch of the branch decision tree for the treatment prior to the alert of the condition. When the caregiver acknowledges that he is finished with the sepsis evaluation, the instance of a primary rules-based service may come out of pause mode, causing the instance of a primary rules-based service to continue navigating through the branch of the branch decision tree to continue the treatment that was ongoing at the time of the disturbance.

Figure 14A:
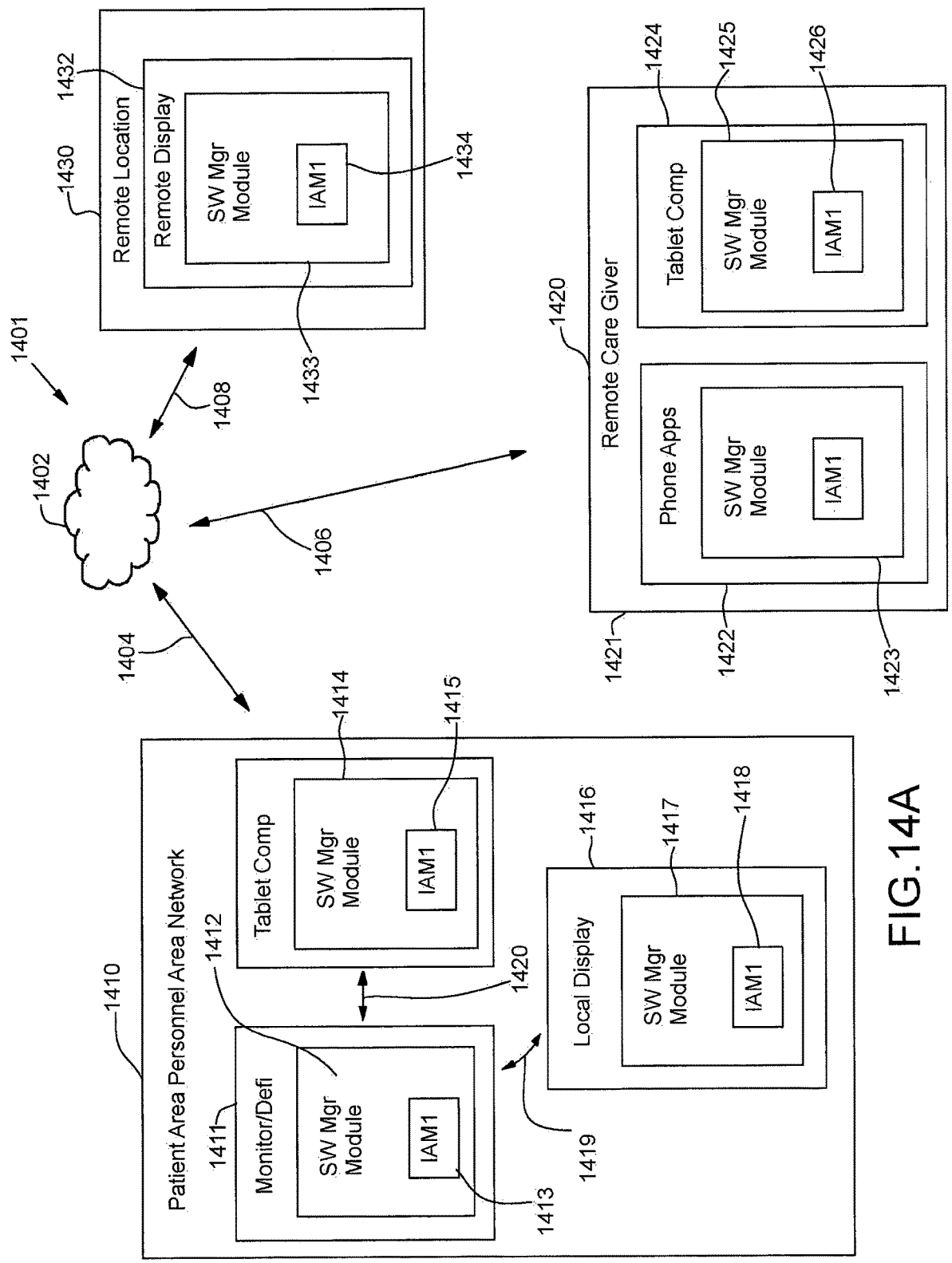
FIGS. 14A and 14B shows further illustrative embodiments of a medical system including a computing architecture of this disclosure.
Figure 14B:
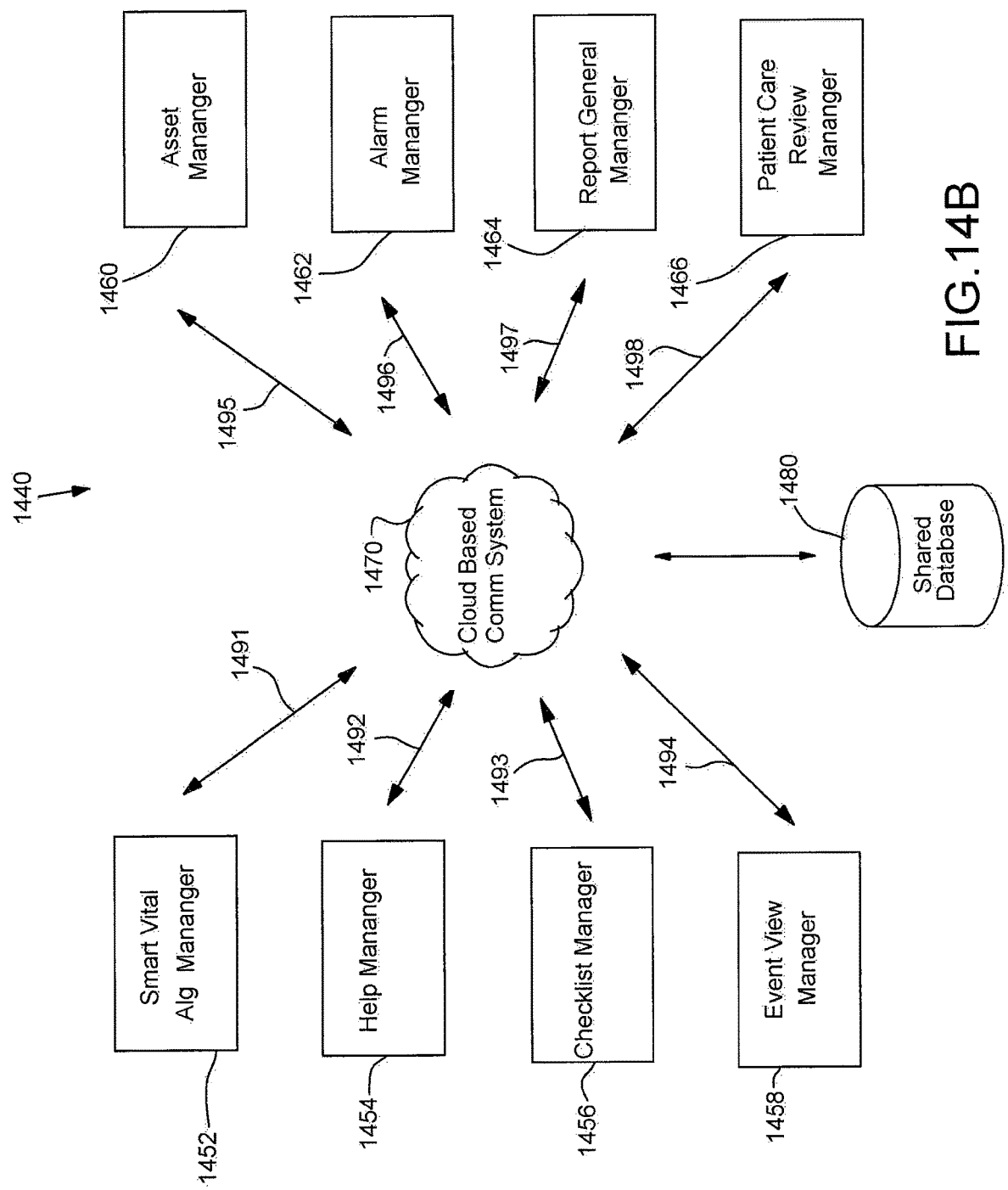

FIGS. 14A and 14B show further illustrative embodiments of a medical system including a computing architecture of this disclosure. FIG. 14A more particularly shows a simplified diagram of a patient care system ("Patient Care System") according to this disclosure. System 1401 includes the devices that are in the patient vicinity 1410 used by the primary care givers and remote viewers ("Remote Viewers") that are used by remote caregivers illustrated as remote caregiver 1420 and remote location 1430 in FIG. 14A. Devices in the patient vicinity 1410 may include a monitor, a monitor/defibrillator, along with Medical Device Software Applications that can operate on a variety of a tablet or PC Computers, and other mobile devices. In a personal area network, they share information directly using various forms of wired or wireless connectivity. To support the Wide Area connection, they may share communications through a cloud-based Internet Communication System 1402. These Software Applications contain various Software Managers (software independent processes) in software manager modules 1412, 1414, 1417 that control the information that is presented to the user on each specific device, and determine what controls and information each user has access to. Information is shared bi-directionally through the system to allow information entered on any Medical Device or Medical Device Software Application to be shared with any other Medical Device in the system. For example, monitor 1411 may communicate with tablet 1413 over communication link 1420 and with local display 1416 over communication link 1419. These devices may each communicate over communication link 1402 through cloud 1402 to reach remote location 1430 and/or remote care giver 1420 or other external utilities. Each Medical Device maintains its own active view of the shared distributed communication system.

FIG. 14B shows a simplified block diagram of a Decision Support system according to this disclosure. Decision Support System 1440 comprises a series of Software Managers shown in FIG. 14B as Smart Vital/Algorithm Manager 1452, Help Manager 1454, Checklist Manager 1456, Event Viewer Manager 1458, Asset Manager 1460, Alarm Manager 1462, Report Generation Manager 1464, and Patient Care Review Manager 1466. The function of these managers has been previously described. Each Software Manager operates independently as part of the user interaction ("User Interaction") solution for the system. Each Manager is responsible for a certain type of information that is provided to one or more users via the User Interface of the specific Medical Device. The actual implementation can include one or more of these Software 38 Managers. Each Software Manager is designed to allow manual input from the user, or the Software Manager may have a series of associated Intelligent Agents which are scanning a shared memory 1480 of the device to determine if a pre-defined inputs or user-configured conditional has occurred and should trigger an action. These pre-defined inputs could include Vital Sign values, Event communications, device state parameters (including identifying sensors disconnected from a patient or not correctly reporting vital sign data), Patient Demographic data, or any of the other categories of shared information communicated across the system. The system may include a cloud based communication system 1470. Communication links 1491-1498 may be established by the associated Software Managers to allow the Software Managers to reach other Software Managers distributed across the network. These distributed Software Managers may reside in remote servers, computers, mobile communicating devices, or the one or more medical devices being used by a caregiver to administer a treatment. The response to a trigger might include displaying a message to the operator, setting a system variable to a pre-defined value, or sending a shared message across the Decision Support system. Any of these outputs could cause another Intelligent Agent within a different Software Manager to trigger an additional response. This secondary response could occur with an Intelligent Agent in the same or different Medical Device within the system.

Software Managers include, but are not limited to a: Checklist Manager, an Event Viewer Manager, a Smart Vitals/Algorithm Manager, Help Manager, an Alarm Manager, a Readiness/Asset Manager, a Report Manager, and a Patient Case Review Manager. These managers have been previously described. Each of these Managers control a type of information that is presented to the User via the device User Interface. Each device in the system contains a Software Application that can run some or all of these Software Managers depending on the type of information presented to the user on that Medical Device type. Additional Software Managers can be added at a later time to provide additional information to the user or Software Managers could be combined in any form.

The Intelligent Agents are self-contained, reactive, and associated with the various Software Managers. They operate independently of the main threads of these Software Managers. They are interconnected via a shared distributed communication system that supports both the Medical Devices and Remote Viewers. The Intelligent Agents have execution dispatched by the operating system, by operating system middleware, or by an execution engine. Intelligent Agents independently process the shared information received and if the right values, combination and sequence of inputs are received to match the user pre-defined conditional, encapsulated within the agent, they trigger a pre-programmed response by their associated Software Manager. Example responses to triggers include generating alarms, sending messages, logging events, activating or deactivating sensors or actuators, initiating user input or output, or any other action deemed appropriate by the software manager's implementation. The response to a trigger could also be a change in the contents of shared memory, which may in turn lead other Intelligent Agents from the same or different Software Managers to trigger and initiate additional actions. The reacting agents may be within Software Managers that are located locally on the Medical Devices, or on one of the Remote Viewers of the system, allowing a coordinated response to patient care across a local area (such as within an ambulance or hospital room) or broad geographical area (such as within the area served by an EMS organization, hospital group, or collection of care givers within a region).

Both system agents and user-configurable agents are allowed. System agents are fixed within the system as part of the design, and usually used to ensure safe operation of the device or to alert the necessary personnel in case of problems. The user-configurable Intelligent Agents are more focused on the patient, and are configurable by the Medical Director (Customer) to create the sequence of inputs and trigger actions that they want to occur in the specific Software Managers across the various Medical Devices.

When configuring an Intelligent Agent, customers can decide what Manual Inputs and shared data are available to stimulate the Agent and what specific response the Agent will trigger within the associated Software Manager. The data may include both instantaneous events or data readings, as well as state information (such as mode of the system) or historical data (e.g. data trending). The specific response and what is displayed to the user may also be tailored by the Medical Director. In this manner, the Medical Director has full control over what aspects of the Decision Support System they want to implement, and what specific outputs are provided by the Software Managers when Intelligent Agents trigger within the Medical Device. The Medical Director can implement as little or as much of this system as they see fit.

To accomplish this customer tailoring, the Decision Support System includes a Decision Support Definition Editor that can be used by the Medical Director to create this customization. The Decision Support Definition Editor allows the Medical Director to create the list of Intelligent Agents, and their Manual Inputs, action trigger and resulted User Interface presentation. The Editor allows the Medical Director to specify which instances of the Software Manager this specific Intelligent Agent is to work with.

The Intelligent Agents are illustratively architected to be Meta data-driven, so that no code ever needs to be compiled when a customer creates a configuration. Thus the Decision Support Definition Editor creates a Decision Support Definition Set that can be downloaded to each allocated device. This Support Tool Software Set could be implemented using a markup language such as XML, or implemented in some other type of Meta Data structure. The Intelligent Agents configure themselves based on the Medical Device configuration, and execute according to the needs of the configuration. Through this process the user can decide what specific inputs and data are available, how the device responds to those inputs and data, and exactly what action is produced, including control what is displayed on the screen, what messages get sent, what data or events get logged, what lights get controlled, and what sensors and actuators get activated or deactivated.

Figure 15A:
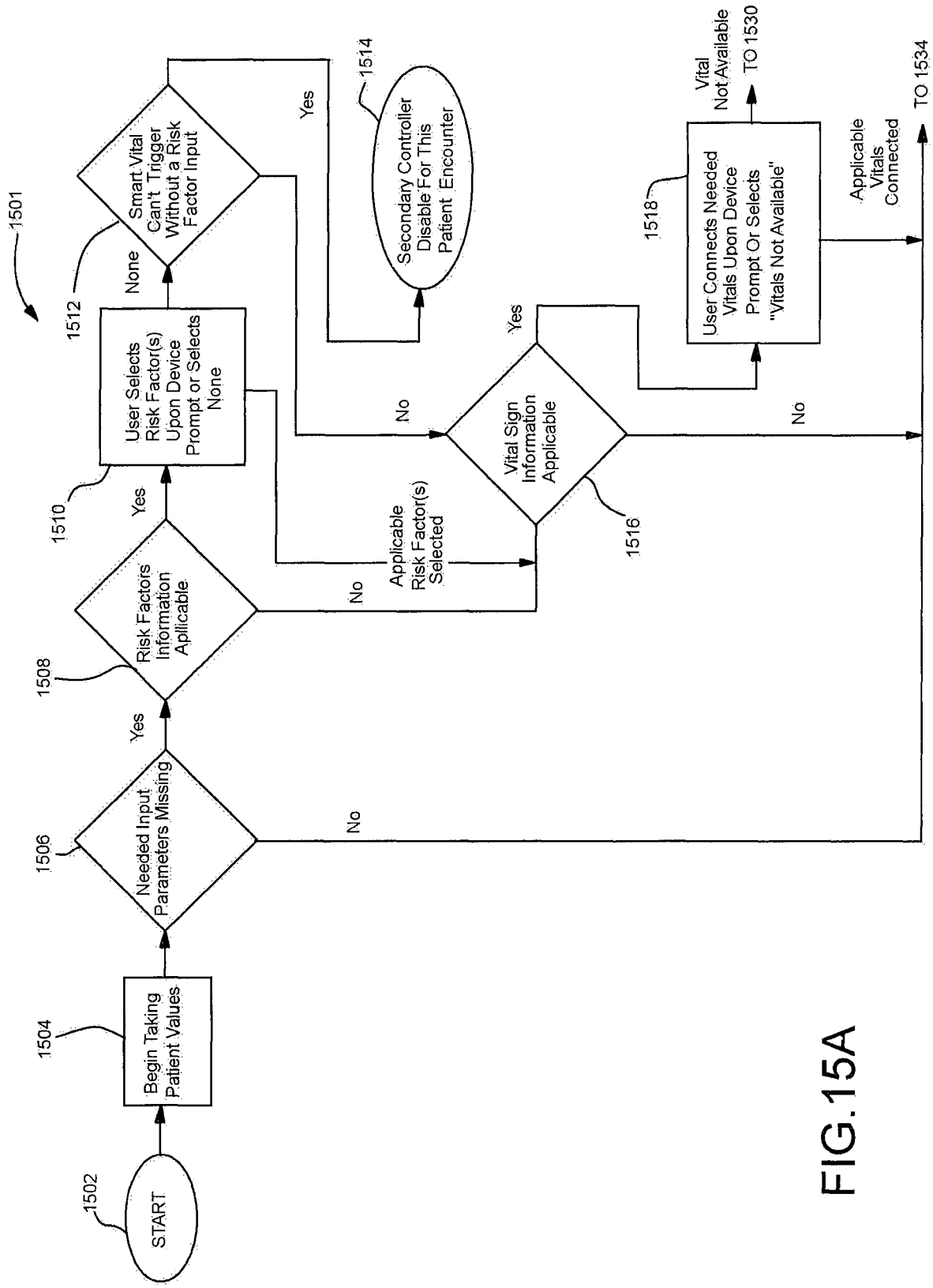
FIGS. 15 A-C show an illustrative embodiment of a process for the artificial intelligence architecture of this disclosure.
Figure 15B:
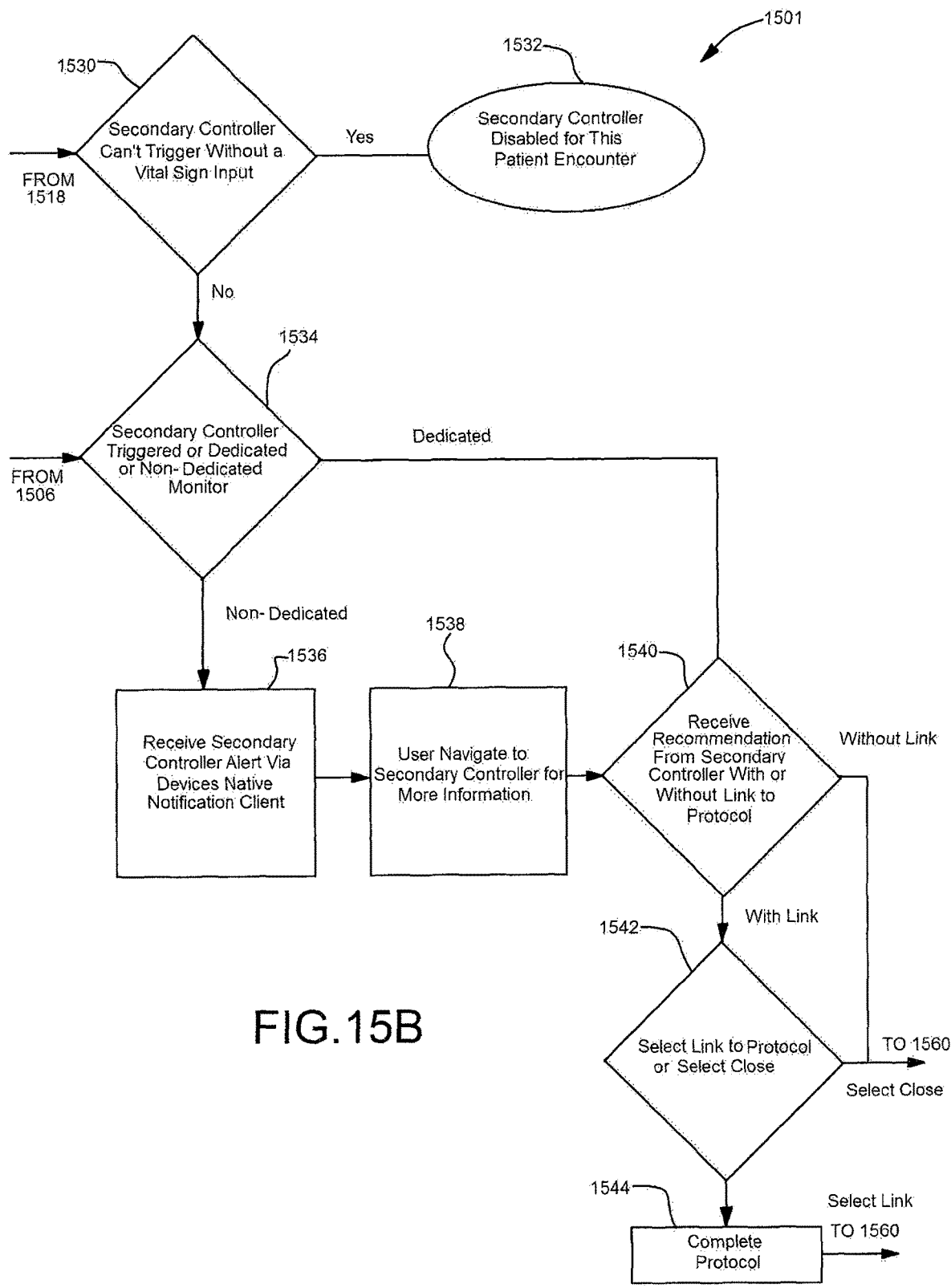
Figure 15C:
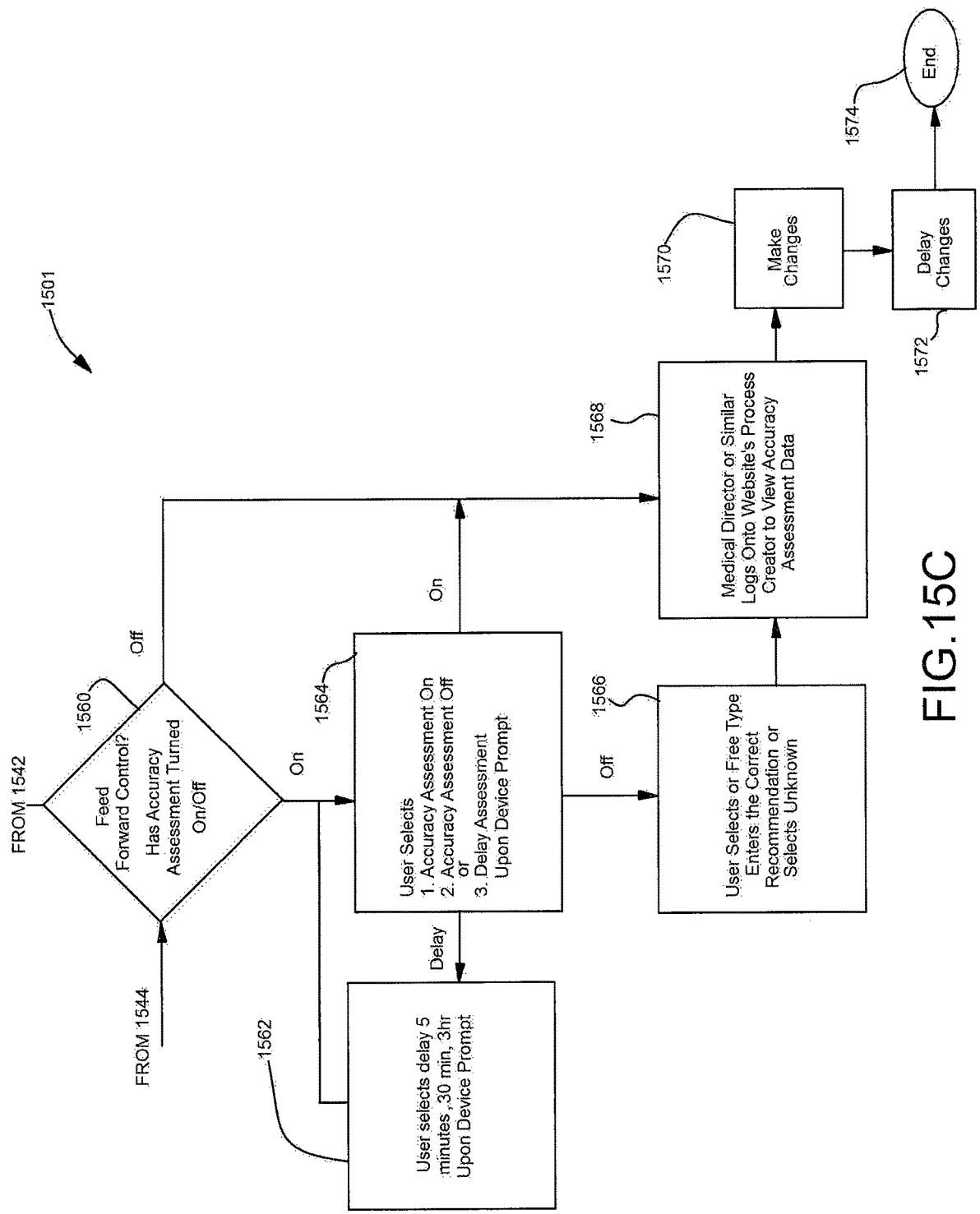

FIGS. 15A, 15B, and 15C show an illustrative example of the decision support system of this disclosure. As shown in FIG. 15A, the process begins at start 1502. At step 1504, the process begins taking patient values The patient values may be patient parameter values such as $CO_2$ exhaled by a patient; electrical activity of the heart of a patient; exchange of air between the lungs of a patient and the atmosphere; pressure of the blood in a patient; temperature of a patient; oxygen saturation in the blood of a patient; chest compression of a patient; image of the internal structure of a patient; oxygen saturation in the blood in the brain of a patient; acidity or alkalinity of fluids in a patient; or other patient parameter. The methods for measurement of these patient parameters have been previously described. The patient values may also be values that are input by a user such as risk factors denoted in step 1508. At step 1506, the process determines if input parameters are missing. If they are not missing the process advances to step 1534 shown in FIG. 15B. If they are missing the process advances to step 1508 to determine if risk factor(s) information is applicable. Risk factors are values selected or input by the user that denote the level of risk of a certain event, such as the risk of heart disease. These may include sex, age, family history of heart disease, post-menopausal, race, smoking, cholesterol level, obesity, etc. If they are not applicable the process advances to step 1516 described below. If they are applicable, at step 1510, the user selects the risk factors upon device prompt or selects none. If applicable risk factor(s) are selected the process advances to step 1516 described below. If the user selects none, at step 1512, the process determines whether it can trigger without a risk factor input. If it can trigger without a risk factor input, at step 1514, the process disables the secondary controller or processing thread of the artificial intelligence architecture for this patient encounter. If it can trigger without a risk factor input the process advances to step 1516. At step 1516, the process determines whether vital sign information is applicable. If vital sign information is not applicable, the process advances to step 1534 shown in FIG. 15B. If vital sign information is applicable, the process advances to step 1518. At step 1518, the user connect needed vitals upon device prompt or selects "vital not available." The connections the user would be made are those required to determine the patient parameters or vitals that are needed for the particular treatment being processed. If vitals are not available, the process advances to step 1530 shown in FIG. 15B. Otherwise, the process advances to step 1534 shown in FIG. 15B.

Referring to FIG. 15B, at step 1530, the process determines whether the secondary controller or processing thread of the artificial intelligence architecture cannot trigger without a vital sign input. If the secondary controller or processing thread of the artificial intelligence architecture can trigger without a vital sign, the process advances to step 1532, where the secondary controller or processing thread of the artificial intelligence architecture is disabled for this patient encounter. If the secondary controller or processing thread of the artificial intelligence architecture cannot trigger without a vital sign, the process advances to step 1534, where the process determines whether the secondary controller or processing thread of the artificial intelligence architecture is to be triggered on a dedicated or non-dedicated unit. A dedicated unit may be the user interface 370 described in FIG. 3 or it may be a user interface on another computing device which is configured with a secondary controller or processing thread of the artificial intelligence architecture client, also referred to herein as a Native Notification Client, for receiving secondary controller alerts. If the secondary controller or processing thread of the artificial intelligence architecture is to be triggered to a dedicated unit, the process advances to step 1540. If a non-dedicated monitor is to be used, the process advances to step 1536 where the process is configured with the settings for the Native Notification Client of the non-dedicated unit and at step 1538 the user navigates to the secondary controller or processing thread of the artificial intelligence architecture for more information. At step 1540, the process determines whether it will be receiving recommendations from the secondary controller or processing thread of the artificial intelligence architecture with or without a link to a protocol. If it will receive recommendations without a link to a protocol, the process advances to step 1560 in FIG. 15C. If it will receive recommendations with a link to a protocol, at step 1542, the user selects the link to a protocol or selects close. If the user selects close, the process advances to step 1560 in FIG. 15C. If the user selects link to a protocol, the process advances to step 1544 where the complete protocol is linked to the process after which the process advances to step 1560 in FIG. 15C.

Referring to FIG. 15C, at step 1560, the process determines whether the artificial intelligence is to be adapted, also referred to herein as Accuracy Assessment. If the Accuracy Assessment is turned off, the process advances to step 1568 described below. If the Accuracy Assessment is turned on, the process advances to 1564 where a user selects whether to keep the Accuracy Assessment on, turn it off, or delay the enablement of the Accuracy Assessment. If the delay is selected, the process advances to step 1562 where a user selects a period of time to delay the enablement of the Accuracy Assessment. The delay may be 5 minutes, 30 minutes, 3 hours, some other period of time, or upon a device prompt such as by a user. The delay introduces a delay in the enablement of the Accuracy Assessment for the selected period of time. On time-out, the process returns to step 1564 to determine whether another delay is needed or whether the process may continue with the Accuracy Assessment being enabled or disabled. If at step 1564, the user selects the Accuracy Assessment to be disabled the user the process advances to step 1566 where the user selects or free type enters the correct recommendation to make or selects unknown. The recommendations entered would be the corrections that a user might make to the decision support system 1401 shown in FIGS. 14A, 14B based upon operation of the process. An unknown recommendation might be a situation where an error was observed by the user but the user may think of no recommendation to make to correct the error. An unknown recommendation may also be important since as previously explained, these outputs are provided to an administrator of the decision support system 1401 shown in FIGS. 14A, 14B by wired or wireless techniques, who may have the expertise to make a recommendation to correct the error based upon experience, information, or data. For example, the administrator may compare the error to historic data on the process flow such as data collected from medical devices using the processes which may be stored in a database. As another example, the administrator may research authorities for information on how to correct the error that may unknown to the user.

At step 1568, an administrator such as a medical director may log onto a website's process creator to view Accuracy Assessment Data. At step 1570, the administrator may make changes to the process. At step 1572, the administrator may deploy those changes to the medical device 1420 in FIG. 14 and/or one or more similar devices that are being administered by the administrator. This completes the adapting of the artificial intelligence as previously explained and ends the process at step 1574.

Figure 16A:
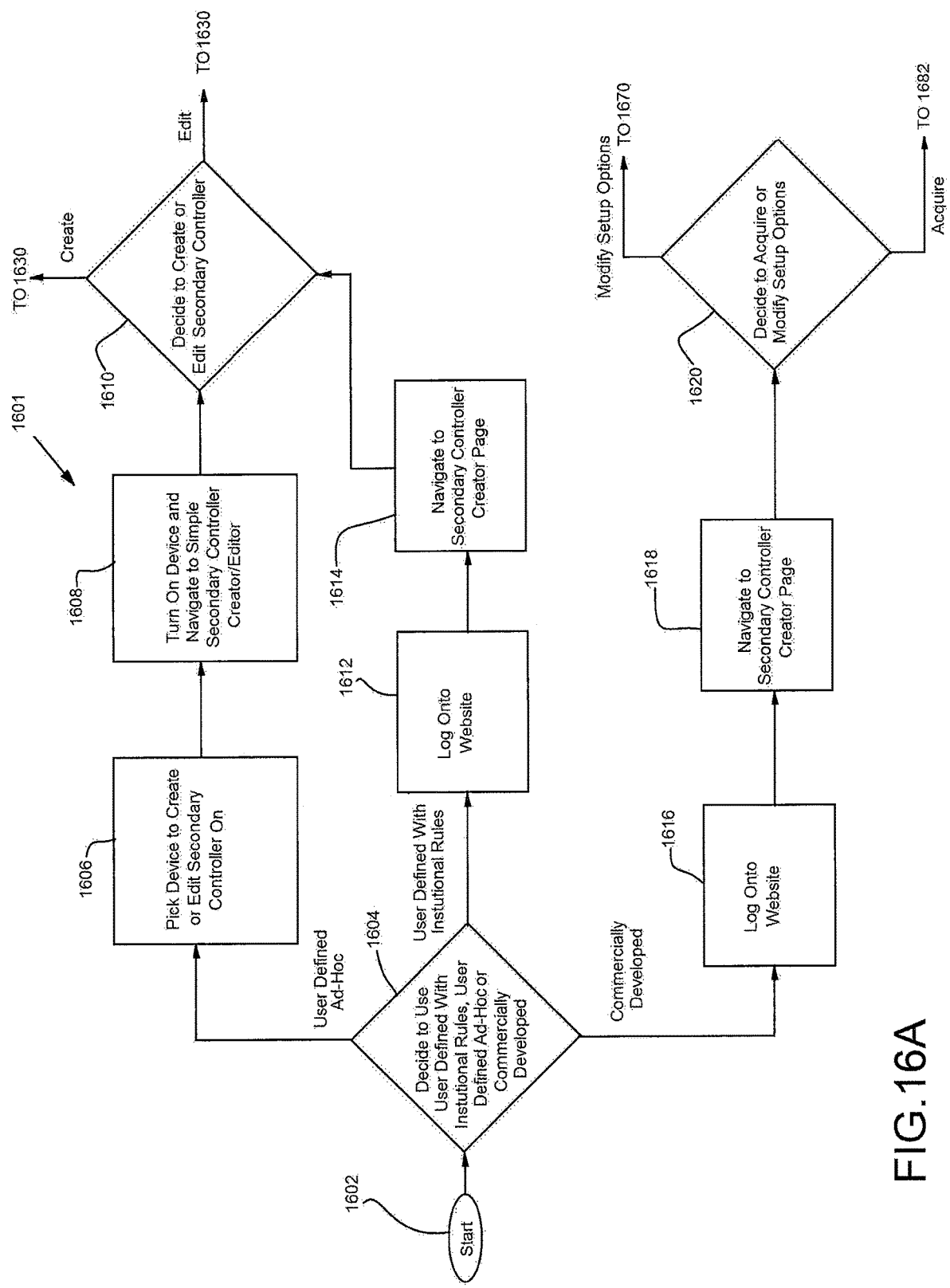
FIGS. 16 A-C is an illustrative embodiment of a process for the creation and distribution of artificial intelligence constructs, and/or updates thereto, to medical devices according to this disclosure.
Figure 16B:
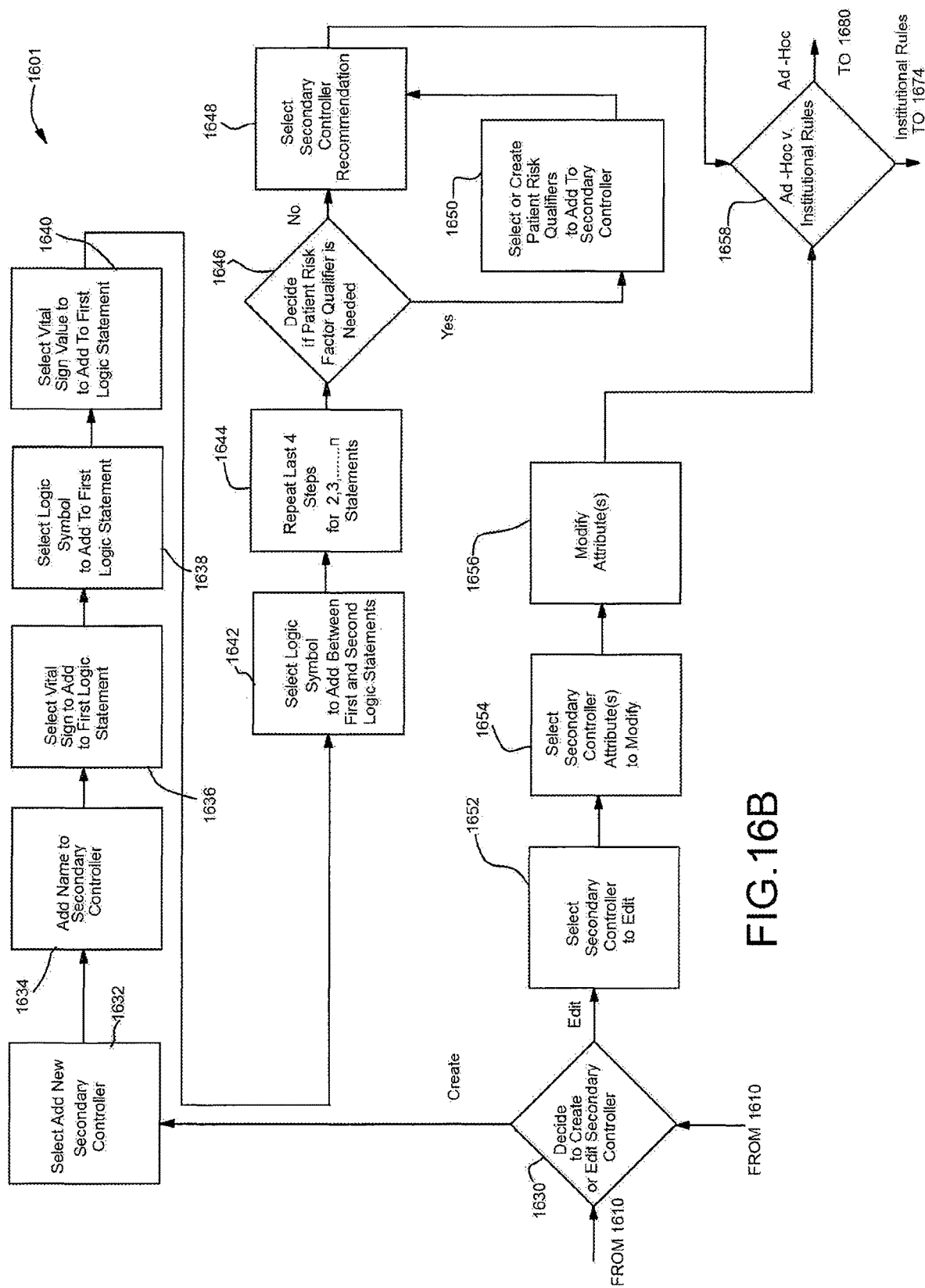
Figure 16C:
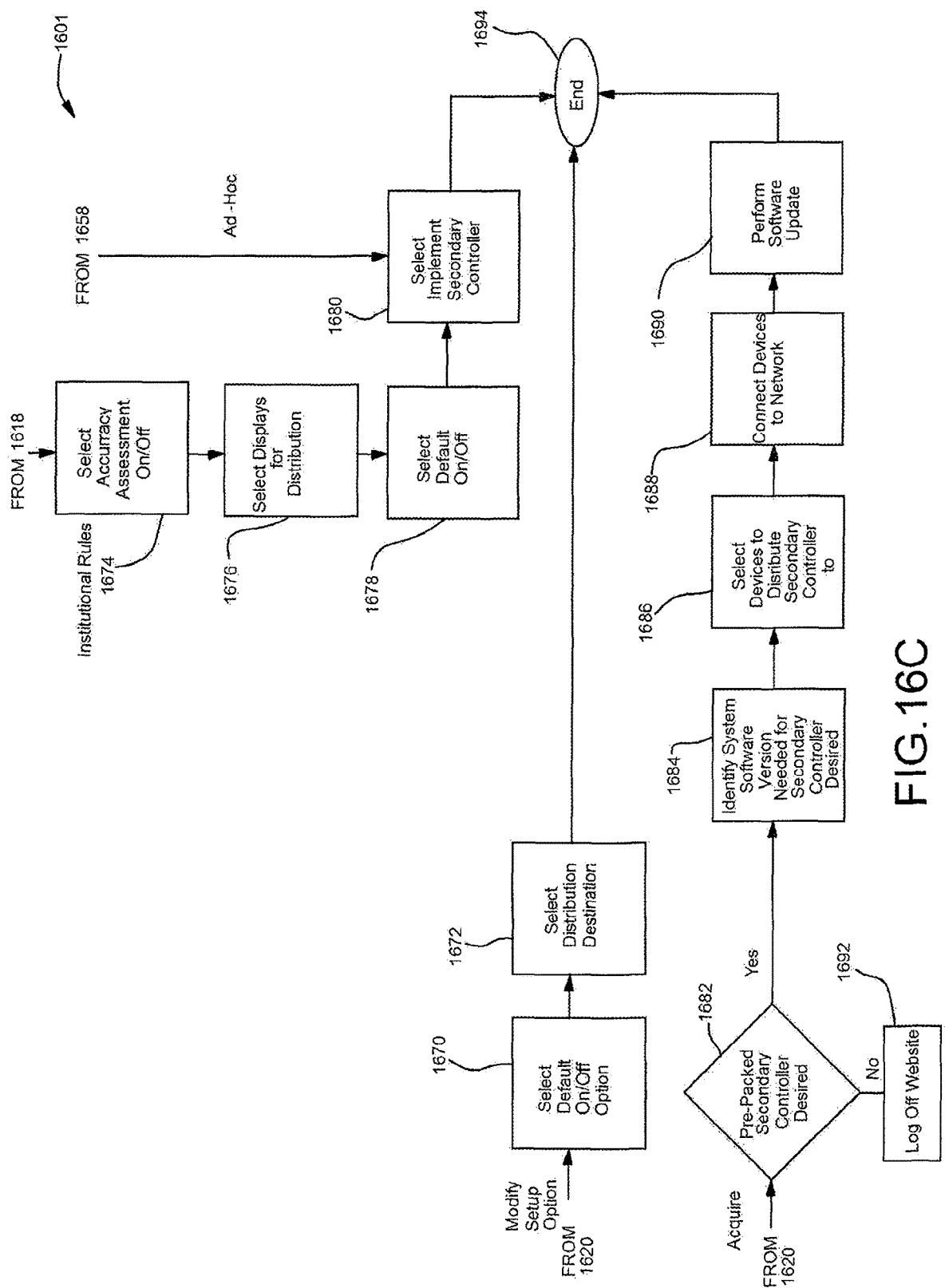

FIGS. 16A, 16B, and 16C show a process for creating processes for use in the decision support system of this disclosure, deploying the processes to one or more medical devices, and making and deploying changes to any deployed process whether triggered by the adaptive intelligence of the artificial intelligence architecture of this disclosure in use or by an update of a process by the administrator. Referring first to FIG. 16A, the process begins at step 1602 and advances to a step 1604 where a decision is made whether to use administer defined Ad-hoc rules, administer defined institutional rules, or use commercially developed rules in the process to be deployed. If an administrator defined Ad-hoc rule is selected the process advances to step 1606 where the administrator selects one or more devices to create or edit a secondary controller on. At step 1608, the administrator turns on the device and navigates to a simple secondary creator editor. At step 1610, the administrator decides to create or edit the secondary controller. If create is selected, the process advances to step 1630. If edit is selected, the process advances to step 1630.

If, at step 1604, the administrator selects institutional rules for the process, at step 1612, the administrator illustratively logs onto a website of institutional rules. Alternatively, the administrator may collect that information from other sources. At step 1614, the administrator navigates to the second controller or processing thread of the artificial intelligence architecture creator page which takes the process to step 1610 previously described.

If at step 1604, the administrator selects commercially developed rules for the process, at step 1616, the administrator logs on a website of commercially developed rules or collects that information from other sources. At step 1618, the administrator navigates to the second controller or processing thread of the artificial intelligence architecture creator page. At step 1620, the administrator decides to acquire or modify the setup options. If modify setup options is selected, the process advances to step 1670. If acquire is selected, the process advances to step 1683.

Referring now to FIG. 16B, at step 1630 the administrator decides whether to create or edit the secondary controller or processing thread of the artificial intelligence architecture. If create is selected, the administrator proceeds to create one or more rules that the secondary controller the artificial intelligence architecture executes such as the following rule for sepsis previously described in connection with FIG. 10.

If ((Evidence of Infection) && ((A&&B) 11 (A&&C) 11 (A&&D) 11 (B&&C) 11 (B&&D) 11 (C&&D)))

The process involves the steps of adding a name 1034, selecting a sign to use for the first logic statement 1636, selecting a logic symbol to add the first logic statement 1638, selecting the vital sign value to add to the first logic statement 1640, selecting the logic symbol to add between first and second logic statements 1642, and repeating steps 1634 through 1642 for each additional logic statement that makes up the rule.

For the above indicated rule for sepsis, and with reference to FIG. 9, starting with rule A&&B above which translates to A AND B, which would be combining rule 920 and rule 922 in a Boolean AND operation, the step of adding a name 1034 would be "temperature and respiratory rate." The step of selecting a sign to use for the first logic statement 1636 would be ">" and "<" in rule 920 and ">" in rule 922. Referring still to FIG. 9, the step of selecting a logic symbol to add to the first rule 920 would be the Boolean OR operation since temperature must be >38 degrees C. or <36 degrees C. For rule 922 there would be no sign to use since the rule requires only that the respiratory rate by > than 20 respirations/minute And to both rule 920 and rule 922 together, the administrator would add the Boolean And operation since this is the Boolean operation required between rule 920 and rule 922 represented as A and B in the following fragment (A&&B) of the above-identified rule for sepsis. The step of selecting the vital sign value to add to the first logic statement 1640 would be "38 or 36" for rule 920 and "20" for rule 922. The step of selecting the logic symbol to add between first and second logic statements 1642 would be the Boolean AND operation represented by && which performs the Boolean AND operation of rule 920 and rule 922 in FIG. 9. The administrator would then repeat steps 1634 through 1642 for each additional logic statement that makes up the rule. In other words, the administrator would do the same for (A&&D), (B&&C), (B&&D), and (C&&D) in the above rule for determining the onset or existence of sepsis.

At step 1646, the administrator decides if a patient risk factor qualifier is needed. If no, the process advances to step 1648 described below. If a patient risk factor qualifier is needed, the administrator selects or creates the patient risk factor qualifiers to add to the secondary controller and advances to step 1650. At step 1648, the administrator selects the secondary controller or processing thread of the artificial intelligence architecture recommendation and advances to step 1648 where the user selects Ad-hoc rules and advances to step 1660 or selects institutional rules and advances to step 1674 both described below.

If at step 1630 the administrator selects edit to edit a secondary controller or processing thread of the artificial intelligence architecture rule that is already part of the process, the creator advances through steps 1652, 1654, and 1656 where the administrator selects the secondary controller or processing thread of the artificial intelligence architecture rule to edit, selects the attributes of the rule to modify, and modifies the attributes, respectively. The process then advances to step 1658 for the administrator to select whether to use Ad-hoc or institutional rules as previously described.

Referring finally to FIG. 16C, when coming the institutional rules branch of step 1658 of the branch for using administrator defined ad hoc rules or user-defined with institutional rules branch (see step 1604 on how to enter those branches), at step 1674 the administrator selects the Accuracy Assessment, which is the adapting of the artificial intelligence, on/off. At step 1676, the administrator selects the distribution destinations, at step 1678, the administrator selects whether to have any defaults on or off, at step 1680, the administrator selects implementation of the secondary controller, which transmits the changes to the selected controller(s) or processing thread of the artificial intelligence architecture wirelessly or by wire, after which the process ends at step 1694.

When coming from the modify branch of step 1620 of the branch for using commercially developed rules (see step 1604 on how to enter that branch), at step 1670, the administrator selects the default on/off option, and at step 1672, which distribution destinations to send the secondary controller or processing thread of the artificial intelligence architecture to, which transmits the changes to the selected controller(s) or processing thread of the artificial intelligence architecture wirelessly or by wire, after which the process ends at step 1694.

When coming from the acquire branch of step 1620 of the branch for using commercially developed rules (see step 1604 on how to enter that branch), at step 1682, the administrator determines whether a pre-packaged secondary controller or processing thread of the artificial intelligence architecture is desired. If none is available, the administrator logs off the website at step 1692. If a prepackaged secondary controller or processing thread of the artificial intelligence architecture is available, at step 1684, the administrator identifies the system software version needed for the secondary controller or processing thread of the artificial intelligence architecture desired. At steps 1686, 1688, and 1690, the administrator identifies the devices to distribute the secondary controller or processing thread of the artificial intelligence architecture to, connects those devices to the network, and performs a software update, respectively. The process ends at step 1694.

From the foregoing it is seen that a computing architecture, system and method are disclosed for use in a medical device for providing decision support to a caregiver. The computing architecture includes a memory, a processor in communication with the memory, and an instance of a primary rules-based service configured to provide instruction events, the instance providing a primary processing thread of instruction events for coaching treatment of a patient. A software manager module includes an artificial intelligence architecture. The artificial intelligence architecture is configured to provide an instance of a conditional rules-based service for providing instruction events. The instance provides a processing thread of instruction events for coaching treatment of a patient that is independent of the primary processing thread and is configured to trigger an action on the occurrence of a pre-defined set of input conditions.

The artificial architecture may be an intelligent agent configured with a conditional rule. The artificial architecture may be a rule engine configured with a conditional rule. The artificial architecture may be an expert system configured with a conditional rule.

The instance of a conditional rules-based service may be configurable by an administrator of the computing architecture. The configurability of the medical device may enable the administrator to configure the conditional rules-based service to a particular environment. The configurability of the medical device may enable the administrator to configure the conditional rules-based service to provide a particular user interface response. The configurability of the medical device may enable the administrator to configure the conditional rules-based service to operate on a set of distributed, interconnected medical devices. The set of distributed, interconnected medical devices support a plurality of system configurations. The configurability of the medical device may enable the administrator to configure the conditional rules-based service to cover a predetermined number of patient conditions. The configurability of the medical device may enable the administrator to configure the conditional rules-based service to cover a predetermined number of treatment paths.

The medical device may further include a decision support definition editor configured to provide the instance of a conditional rules-based service for providing instruction events.

The medical device may further include a user interface and a software manager responsible for triggering a predetermined action on the user interface. The user interface may be a display; and the predetermined action on the user interface is a rendering information on the display. The artificial intelligence architecture of the software manager module of the medical device may be further configured to provide one or more additional instances of a conditional rules-based service for providing instruction events, the one or more additional instances providing one or more additional processing threads of instruction events for coaching treatment of a patient that are independent of the primary processing thread and are configured to trigger an action on the occurrence of a pre-defined set of input conditions.

The medical device may further include a user interface. The user interface may be configured for receiving input data for configuring the computing architecture. The intelligent agent may be configured to scan the memory of the medical device to determine if a predefined input or a user configured condition has occurred and should trigger an action.

The software manager module may provide a first software manager; and may further include a second software manager module including an artificial intelligence architecture. The artificial intelligence architecture may be configured to provide an instance of a conditional rules-based service for providing instruction events. The instance may provide a processing thread of instruction events for coaching treatment of a patient that is independent of the primary processing thread and is configured to trigger an action on the occurrence of a pre-defined set of input conditions. The artificial architecture of the second software manager module may be an intelligent agent configured with a conditional rule. A predefined input or a user configured condition may trigger an action by the second software manager module. The first software manager module may trigger a first action; and the first action may be applied to the second software manager module to trigger a second action.

The software manager module may include a software manager selected from the group consisting of smart vital algorithm manager, a help manager, a checklist manager, an event viewer manager, an asset manager, an alarm manager, a report generator manger, and a patient care preview manager. The instance of a conditional rules-based service for providing instruction events may be for detection of sepsis. The instance of a conditional rules-based service for providing instruction events may include a set of rules including:

if ((Evidence of Infection) && ((A&&B) 11 (A&&C) 11 (A&&D) 11 (B&&C) 11 (B&&D) 11 (C&&D)))

wherein:

A=Temperature>38 degrees C. or <36 degrees C.
B=Respiratory rate>20 respirations/minute
C=Heart Rate>90 beats/min
D=White Blood cell count>12×10^9/L or <4×10^9/L or with >10% immature forms &&=the Boolean logical operator AND
11=the Boolean logical operator OR The instance of a conditional rules-based service for providing instruction events may include a device alert. The device alert may be rendered on a display of a device selected from the group consisting of a smart phone; a lap top, a notebook, a PDA, a personal computer, a monitor, and any computing device.

A medical system of this disclosure may include a medical device, an instance of a primary rules-based service, a software manager module, and an external utility. The medical device may include a computing architecture. The computing architecture may include a memory, a processor in communication with the memory, and a communication module. The instance of a primary rules-based service may be configured to provide instruction events. The instance may provide a primary processing thread of instruction events for coaching treatment of a patient. The software manager module may include an artificial intelligence architecture. The artificial intelligence architecture may be configured to provide an instance of a conditional rules-based service for providing instruction events. The instance may provide a processing thread of instruction events for coaching treatment of a patient that is independent of the primary processing thread and is configured to trigger an action on the occurrence of a pre-defined set of input conditions.

The external utility may be in communication with the medical device. The external utility may be configured for exchanging data between the medical device and the external utility.

The medical system may further include a shared data base. A software manager may be provided. The software manager may be selected from the group consisting of a smart vital algorithm manager, a help manager, a checklist manager, an event viewer manager, an asset manager, an alarm manager, a report generator manger, and a patient care preview manager. The software manager may be configured to access the shared database.

The external device may be a computer. The computer may be a server. The communication between the medical device and the external device may be via a network. The network may be the Internet.

The external device may be a computer selected from the group consisting of a server, a personal computer, a tablet, a mobile computing device, a video device, an ultrasound device, and a printer. The external device may be in communication with the medical device through an access point. The communication from the external device is by an intelligent agent; the intelligent agent providing interpretation of data from the medical device. The communication from the medical device may be to an asset management registry intelligent agent, the asset management registry agent configured to manage assets of the system. The communication from the external device may be by decision support server.

A method for providing decision support for a medical treatment may include the steps of providing a primary processing thread of instruction events for coaching treatment of a patient based on a primary rules-based service; providing a processing thread of instruction events for coaching treatment of a patient that is independent of the primary processing thread for coaching treatment of a patient based on a conditional rules-based service; triggering an action by the independent processing thread of instruction events based on a conditional rules-based service on the occurrence of a pre-defined set of input conditions.

The method may further include the step of configuring the instance of a conditional rules-based service by an administrator. The configurability of the medical device may enable the administrator to configure the conditional rules-based service to a particular environment. The configurability of the medical device may enable the administrator to configure the conditional rules-based service to provide a particular user interface response. The configurability of the medical device may enable the administrator to configure the conditional rules-based service to operate on a set of distributed, interconnected medical devices.

The set of distributed, interconnected medical devices of the method may support a plurality of system configurations. The configurability of the medical device may enable the administrator to configure the conditional rules-based service to cover a predetermined number of patient conditions. The configurability of the medical device may enable the administrator to configure the conditional rules-based service to cover a predetermined number of treatment paths.

The method may further include the step of configuring the conditional rules-based service for providing instruction events. The method may further include the step of triggering a predetermined action on a user interface based upon the action triggered by the independent processing thread of instruction events. The user interface used in the method may be a display. The predetermined action on the user interface may be a rendering information on the display.

The method may further include the step of triggering a predetermined action on a user interface by a software manager. The software manager may be selected from the group consisting of smart vital algorithm manager, a help manager, a checklist manager, an event viewer manager, an asset manager, an alarm manager, a report generator manger, and a patient care preview manager. The instance of a conditional rules-based service for providing instruction events may be for detection of sepsis. The instance of a conditional rules-based service for providing instruction events may include a device alert. The device alert may be rendered on a display of a device selected from the group consisting of a smart phone; a laptop, a notebook, a PDA, a personal computer, a monitor, and any computing device.

The method may further include the step of transmitting the triggered action to an external utility. The external device may be a computer. The computer may be a server. The communication between the medical device and the external utility may be via a network. The network may be the Internet. The external device may be a computer selected from the group consisting of a server, a personal computer, a tablet, a mobile computing device, a video device, an ultrasound device, and a printer.

The artificial intelligence architecture of this disclosure provides device driven recommendations of a patient's health and care path that are based on mathematical assessments of multiple input parameters such as physiological vital signs and health related risk factors. They may improve caregiver response time, alarm accuracy, and to aid in giving caregivers ideas of potential next steps. The computing architecture of this disclosure provides a Decision Support System using Intelligent Agents that are distributed across multiple devices through shared Communications. The Decision Support System is Modular, made up of a series of Intelligent Agents (or other conditional rules engine) that may run within Software Managers. The Decision Support System is interconnected through a series of bidirectional distributed shared Communications.

The Decision Support System is available to run on many different Medical Devices across distributed system. The Decision Support System may support a wide variety of Medical Device configurations. The Decision Support System may operate on integrated devices working in a Local Area or on remote devices that are supported through our Cloud Based Internet System. The Decision Support System may include system rules programmed into each individual device. The Decision Support System may be tailored by the Customer (End User) to determine which parts run on which device.

The Decision Support System may be tailored by the Customer to determine which elements to include, what manual inputs are provided, what triggers are included and exactly what appears on the screen (checklists, messages, reference material, etc.). The Decision Support System may be used to support a broad range of patients who are experiencing a vast array of Medical Emergencies and the supporting treatment paths for each of these emergencies.

This disclosure extends the current state-of-the-art for Medical Device Decision Support systems. Medical Device Decision Support systems that currently exist typically operate on a single set of Medical Emergencies, with treatment paths editors that are specific to a predefined configuration of Medical Devices. This disclosure is unique in form, by creating a simplified Decision Support System that is modular, interconnected, and can fully be tailored to the needs of many Customers.

This use of a series of integrated Intelligent Agents allows a Decision Support System that may be customized to work on a broad set of distributed inter-connected Medical Devices supporting numerous system configurations. This Decision Support System is applicable to a broad set of Medical Emergencies, covering a number of patient conditions and supporting treatment paths.

The Decision Support System of this disclosure may use multiple physiological patient parameter input data to trigger a device response. The Decision Support System may analyze user (clinician, medical director, etc., entered patient risk factors, patient demographic information, and/or past patient event data to trigger the device response. The user may create the rules, including the physiological patient parameters, the parameters' trigger values, and the applicable patient risk factors, patient demographic information, and/or past patient event data to be considered. The decision controller may trigger a device response that provides a caregiver with notification of the rule triggered. The Decision Support System response may include a patient diagnosis. The Decision Support System response may include a recommended course of action for the clinical user to consider taking in respect to the patient. The Decision Support System response may be communicated remotely from the patient to a personal computer, a tablet, a smart phone, a server, or other computing device.

In the adaptive intelligence part of this disclosure a user is requested to enter an accuracy assessment of the Decision Support System response compared to the actual patient condition. The user entered "accuracy assessment(s)" may be used to make a recommendation to the caregiver of a parameter or device response that could be changed to improve the accuracy of the decision tree controller in the future. The user entered "accuracy assessment(s)" may be used to automatically update the decision tree controller. Multiple "accuracy assessments" across many patients and separate institutions may be used to make changes to the algorithms parameters or device response to improve its accuracy. The triggered instruction events and resulting information may be stored as an event in the patient log. The triggered instruction event may cause additional decision support features to be propagated automatically to the user including but not limited to protocol assistant, reminders, etc.

The Decision Support System allows users to enter their own rules that may be specific to their usage needs and as the science matures. The decision tree controller may include additional input parameters over just the common real time monitored physiological parameters. They will leverage user entered patient risk factors. The Decision Support System may give recommendations of a possible course of action for the user to take based on the information received. (e.g., Evaluate Patient for Sepsis). The Decision Support System may be made available to remote viewing at devices such as laptops, tablets, smart phones. The Decision Support System may give the user the ability to assess the accuracy of the instruction event output compared to the actual patient condition post the triggered event. These accuracy assessments may allow for adaptive rule improvements and may allow for more sophisticated rules that can look at extended patient history, trends across patients and the population, etc.

In this description, numerous details have been set forth in order to provide a thorough understanding. In other instances, well-known features have not been described in detail in order to not obscure unnecessarily the description.

A person skilled in the art will be able to practice the present disclosure in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the disclosure may be practiced in combination with other systems. The following claims define certain combinations and subcombinations of elements, features, steps, and/or functions, which are regarded as novel and non-obvious. Additional claims for other combinations and subcombinations may be presented in this or a related document.

We claim:

1. A method for providing decision support for a medical treatment, comprising:
   providing a primary processing thread of instruction events for coaching treatment of a patient based on a primary rules-based service;
   providing a processing thread of instruction events for coaching treatment of a patient that is independent of the primary processing thread for coaching treatment of a patient based on a conditional rules-based service; and
   triggering an action by the independent processing thread of instruction events based on a conditional rules-based service on the occurrence of a pre-defined set of input conditions.

2. The method of claim 1, further comprising configuring an instance of a conditional rules-based service by an administrator.

3. The method of claim 2, wherein the configurability of the instance enables the administrator to configure the conditional rules-based service to a particular environment.

4. The method of claim 2, wherein the configurability of the instance enables the administrator to configure the conditional rules-based service to provide a particular user interface response.

5. The method of claim 2, wherein the configurability of the instance enables the administrator to configure the conditional rules-based service to operate on a set of distributed, interconnected medical devices.

6. The method of claim 5, wherein the set of distributed, interconnected medical devices supports a plurality of system configurations.

7. The method of claim 2, wherein the configurability of the instance enables the administrator to configure the conditional rules-based service to cover a predetermined number of patient conditions.

8. The method of claim 2, wherein the configurability of the instance enables the administrator to configure the conditional rules-based service to cover a predetermined number of treatment paths.

9. The method of claim 8, wherein the instance of a conditional rules-based service for providing instruction events is for detection of sepsis.

10. The method of claim 8, wherein the instance of a conditional rules-based service for providing instruction events includes a device alert.

11. The method of claim 10, wherein the device alert is rendered on a display of a device selected from the group consisting of a smart phone; a lap top, a notebook, a PDA, a personal computer, a monitor, and a computing device.

12. The method of claim 1, further comprising configuring the conditional rules-based service for providing instruction events.

13. The method of claim 1, further comprising triggering a predetermined action on a user interface based upon an action triggered by the independent processing thread of instruction events.

14. The method of claim 13, wherein the user interface is a display, and wherein the predetermined action on the user interface is a rendering information on the display.

15. The method of claim 13, further comprising:
   triggering a predetermined action on a user interface by a software manager,
   wherein the software manager is selected from the group consisting of smart vital algorithm manager, a help manager, a checklist manager, an event viewer manager, an asset manager, an alarm manager, a report generator manager, and a patient care preview manager.

16. The method of claim 1, further comprising transmitting the triggered action to an external utility.

17. The method of claim 16, wherein the external device is a computer.

18. The method of claim 17, wherein the computer is a server.

19. The method of claim 16, wherein communication between the medical device and the external utility is via a network.

20. The method of claim 1, wherein the network is the Internet.

21. The method of claim 1, wherein the external device is a computer selected from the group consisting of a server, a personal computer, a tablet, a mobile computing device, a video device, an ultrasound device, and a printer.

* * * * *